US008333123B2

(12) United States Patent
Tatsutani et al.

(10) Patent No.: US 8,333,123 B2
(45) Date of Patent: Dec. 18, 2012

(54) SAMPLE PROCESSING APPARATUS AND SAMPLE INFORMATION DISPLAY APPARATUS

(75) Inventors: Hiroo Tatsutani, Kobe (JP); Hiroyuki Tanaka, Halstenbek (DE)

(73) Assignee: Sysmex Corporation, Hyogo (JP)

( * ) Notice: Subject to any disclaimer, the term of this patent is extended or adjusted under 35 U.S.C. 154(b) by 478 days.

(21) Appl. No.: 12/606,760

(22) Filed: Oct. 27, 2009

(65) Prior Publication Data

US 2010/0101339 A1 Apr. 29, 2010

(30) Foreign Application Priority Data

Oct. 28, 2008 (JP) ................................ 2008-277438
Feb. 26, 2009 (JP) ................................ 2009-043301

(51) Int. Cl.
*G01N 35/02* (2006.01)

(52) U.S. Cl. .................................................. 73/863.91

(58) Field of Classification Search ................ 73/863.91
See application file for complete search history.

(56) References Cited

U.S. PATENT DOCUMENTS 7,939,021 B2 * 5/2011 Smith et al. ................. 422/68.1
2008/0131318 A1 6/2008 Nakaya

FOREIGN PATENT DOCUMENTS

JP 11-083863 A 3/1999

* cited by examiner

*Primary Examiner* — Hezron E Williams
*Assistant Examiner* — Paul West
(74) *Attorney, Agent, or Firm* — Sughrue Mion, PLLC

(57) ABSTRACT

A sample processing apparatus comprising: a plurality of measuring units, each of which measures a sample; a sample conveyance unit for conveying a sample to at least one of the plurality of measurement units; a display unit; and a display controller for controlling the display unit to display an analysis result of a sample which the analysis result has been obtained based on the measurement by at least one of the plurality of measurement units, and controlling the display unit to display conveyance status information indicating a conveyance status of the sample which analysis result has not been obtained yet based on the measurement by at least one of the plurality of measurement units, is disclosed. A sample information display apparatus is also disclosed.

19 Claims, 34 Drawing Sheets

SAMPLE PROCESSING APPARATUS AND SAMPLE INFORMATION DISPLAY APPARATUS

FIELD OF THE INVENTION

The present invention relates to a sample processing apparatus for conveying a sample to a measurement unit for measuring a sample and a sample information display apparatus for displaying information related to the sample in the sample processing apparatus.

BACKGROUND

Conventionally, a sample processing system, including a plurality of sample processing apparatuses such as a sample analyzer and a smear preparing apparatus and a conveyance device for conveying the sample to each sample processing apparatus is known.

Japanese Laid-Open Patent Publication No. H11-083863 discloses a sample processing system for displaying a rack position in a system configuration diagram displayed on a monitor in real time while distinguishing by the type and quality of the sample. In the sample processing system described in Japanese Laid-Open Patent Publication No. H11-083863, sample information consisting of a sample type, an inserting time, a position, a sample number, a host accepting number and a patient name, are displayed on the monitor by selecting the rack displayed in the system configuration diagram.

However, in the sample processing system described in Japanese Laid-Open Patent Publication No. H11-083863, an analysis result of a sample is not displayed on the monitor, while the sample information described above is displayed on the monitor. Confirming the analysis result of the sample is important to an operator such as inspecting engineer or a doctor. However, in the sample processing system described in Japanese Laid-Open Patent Publication No. H11-083863, an operator needs to display a screen of the analysis result by operating a device capable of displaying the analysis result arranged aside from the sample processing system to confirm the analysis result of the sample, which is very troublesome. When Confirming a conveyance status of a sample, which analysis result has not been obtained yet in the device, the operator needs to return from the device to the sample processing system to confirm the position of the rack displayed on the monitor, which is very troublesome.

SUMMARY

The scope of the present invention is defined solely by the appended claims, and is not affected to any degree by the statements within this summary.

A first aspect of the present invention is a sample processing apparatus comprising: a plurality of measuring units, each of which measures a sample; a sample conveyance unit for conveying a sample to at least one of the plurality of measurement units; a display unit; and a display controller for controlling the display unit to display an analysis result of a sample which the analysis result has been obtained based on the measurement by at least one of the plurality of measurement units, and controlling the display unit to display conveyance status information indicating a conveyance status of the sample which analysis result has not been obtained yet based on the measurement by at least one of the plurality of measurement units.

A second aspect of the present invention is a sample processing apparatus comprising: a plurality of measuring units, each of which measures a sample; a sample conveyance unit for conveying a sample to at least one of the plurality of measurement units; and an information processing unit for displaying information related to a sample including, a display unit, and a controller for executing a process of controlling the display unit to display an analysis result of a sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units.

A third aspect of the present invention is a sample information display apparatus for displaying information related to a sample processed in a sample processing apparatus including a plurality of measuring units, each of which measures a sample, and a sample conveyance unit for conveying a sample to at least one of the plurality of measurement units; the sample information display apparatus comprising: a display unit; and a display controller for controlling the display unit to display an analysis result of the sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units.

DETAILED DESCRIPTION OF THE EMBODIMENT

A preferred embodiment of the present invention will be described with reference to the drawings. The present embodiment relates to a sample processing system equipped with a test information managing device capable of displaying an analysis result and a conveyance status of a sample.

[Configuration of Sample Processing System]

Figure 1:
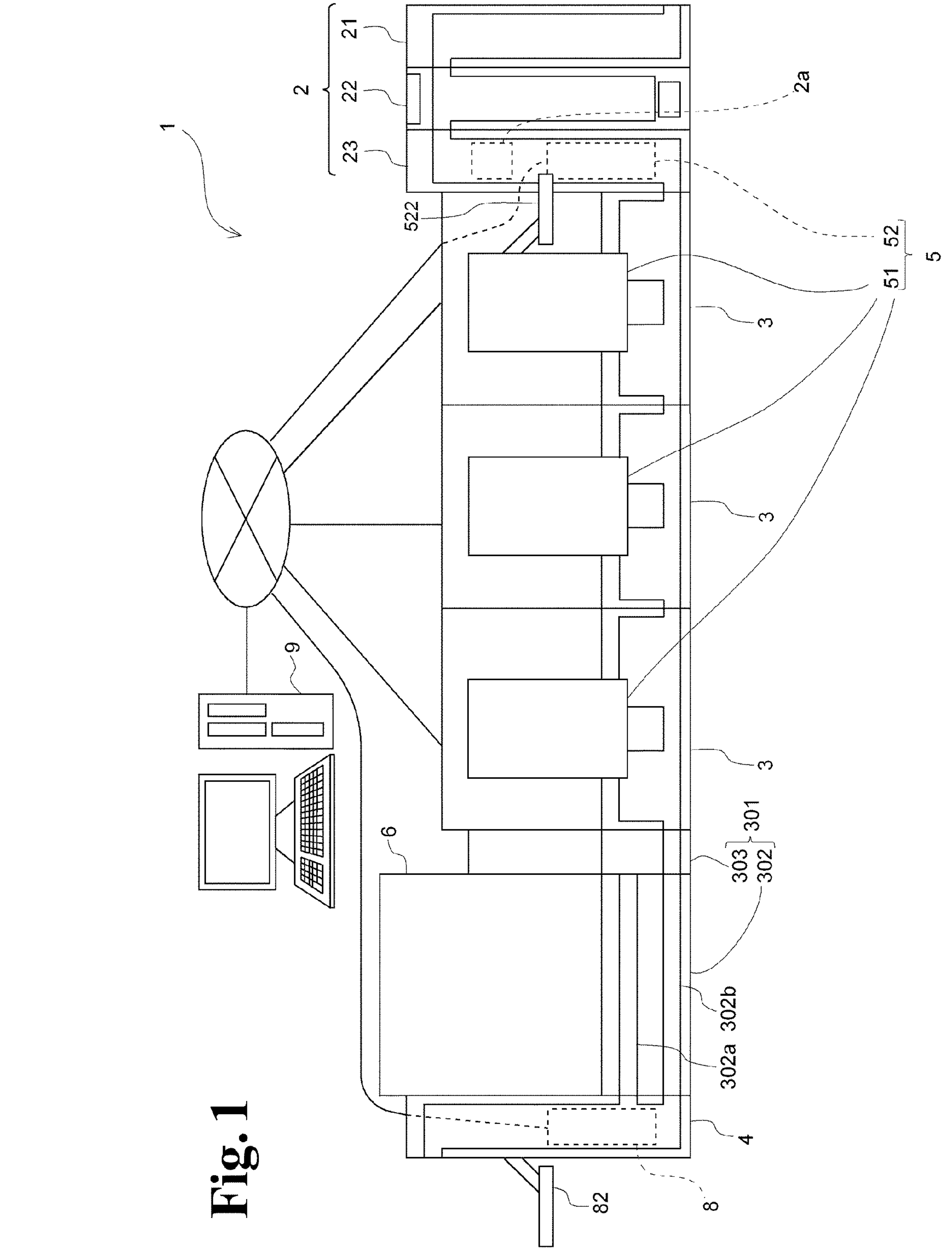
FIG. 1 is a schematic plan view showing an overall configuration of a sample processing system according to an embodiment.

FIG. 1 is a schematic plan view showing an overall configuration of the sample processing system according to the present embodiment. As shown in FIG. 1, the sample processing system 1 includes a sample inserting device 2, sample conveyance devices 3, 301, a sample accommodating device 4, a blood cell analyzer 5, a smear producing device 6, a system control device 8 and a test information managing device 9. The system control device 8 is communicably connected to the test information managing device 9 by way of a communication network.

<Configuration of Sample Inserting Device 2>

The sample inserting device 2 includes a sample inserting unit 21, a barcode reading unit 22 and a sample sending unit 23. The barcode reading unit 22 is arranged between the sample inserting unit 21 and the sample sending unit 23, and is configured so that the sample inserted in the sample inserting unit 21 is transferred to the sample sending unit 23 through the barcode reading unit 22. The sample inserting unit 21 and the sample sending unit 23 are configured such that a sample rack accommodating a plurality of sample containers can be mounted. The sample rack mounted on the sample inserting unit 21 is delivered to the barcode reading unit 22 in order, wherein a rack ID is read from a barcode of a barcode label attached to the sample rack by the barcode reading unit 22, and a sample ID is read from a barcode of a barcode label attached to the sample container. The sample inserting device 2 includes controller 2*a* configured with a CPU and a memory, wherein an operation mechanism of the sample inserting unit 21, the barcode reading unit 22, and the sample sending unit 23 can be controlled by the controller 2*a*. The controller 2*a* of the sample inserting device 2 is communicably connected to the system control device 8 bay way of LAN, and the read rack ID and sample ID described above are transmitted to the system control device 8. The sample rack, which reading of the barcode is terminated, is conveyed to the sample sending unit 23, and sent to the sample conveyance device 3 from the sample sending unit 23.

Figure 2:
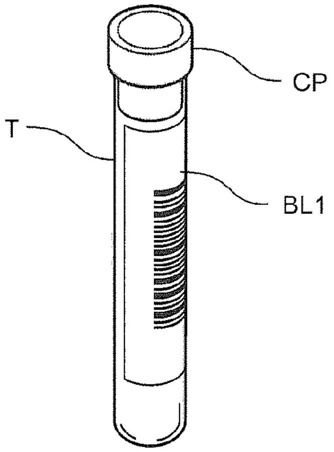
FIG. 2 is a perspective view showing an outer appearance of a sample container.
Figure 3:
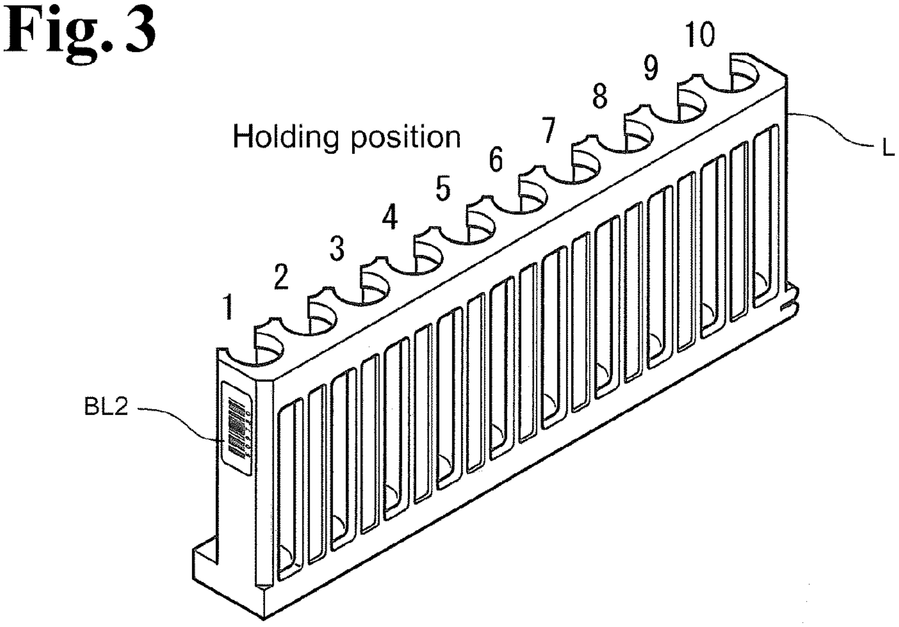
FIG. 3 is a perspective view showing an outer appearance of a sample rack.

FIG. 2 is a perspective view showing an outer appearance of a sample container, and FIG. 3 is a perspective view showing an outer appearance of a sample rack. As shown in FIG. 2, the sample container T has a tubular shape, and the upper end is opened. The blood sample collected from a patient is accommodated therein, and the opening at the upper end is sealed by a lid CP. The sample container T is made of a glass or a synthetic resin having translucency, so that the blood sample inside can be seen. A barcode label BL1 is attached to the side surface of the sample container T. A barcode indicating a sample ID is printed on the barcode label BL1. The sample rack L can hold ten sample containers T side by side. Each sample container T is held in a perpendicular state (standing state) in the sample rack L. A barcode label BL2 is attached to the side surface of the sample rack L. A barcode indicating a rack ID is printed on the barcode label BL2.

<Configuration of Sample Conveyance Device 3>

The configuration of the sample conveyance device 3 will now be described. As shown in FIG. 1, the sample processing system 1 includes three sample conveyance devices 3. The sample conveyance devices 3, 3, 3 are arranged on the front side of three measurement units 51, 51, 51 of the blood cell analyzer 5. The adjacent sample conveyance devices 3, 3 are connected, so that the sample rack L can be exchanged. The sample conveyance device 3 on the rightmost side is connected to the sample inserting device 2 described above, so that the sample rack L carried out from the sample inserting device 2 can be received. The sample conveyance device 3 on the leftmost side is connected to the sample conveyance device 301, so that the sample rack L can be carried out to the sample conveyance device 301.

Figure 4:
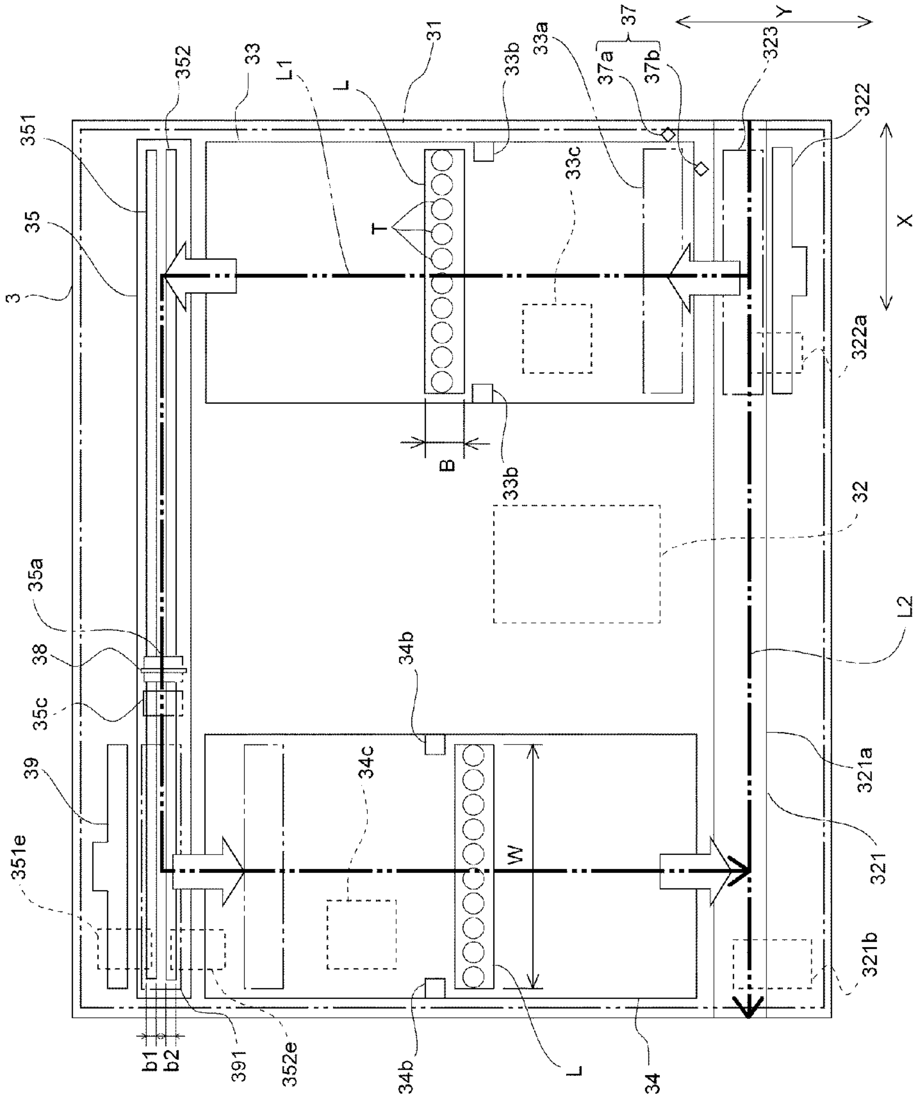
FIG. 4 is a plan view showing a configuration of a sample conveyance device.

FIG. 4 is a plan view showing a configuration of the sample conveyance device 3. As shown in FIG. 4, the sample conveyance device 3 includes a conveyance mechanism 31 for conveying the sample and a controller 32 for controlling the conveyance mechanism 31. The conveyance mechanism 31 includes a pre-analysis rack holder 33 capable of temporarily holding a plurality of sample racks L for holding the sample container T accommodating the sample before the analysis, a post-analysis rack holder 34 capable of temporarily holding a plurality of sample racks L for holding the sample container T from which the sample is aspirated by the measurement unit 51, a rack conveyance portion 35 for moving the sample rack L horizontally and linearly in the direction of the arrow X in the figure to supply the sample to the measurement unit 51 and conveying the sample rack L received from the pre-analysis rack holder 33 to the post-analysis rack holder 34, and a rack conveyance portion 321 for carrying in the sample rack L from the device on an upstream side of conveyance (the sample inserting device 2 or the sample conveyance device 3) and carrying out the sample rack L to the device on a downstream side of conveyance (the sample conveyance device 3 or the sample conveyance device 301) without supplying the sample accommodated in the sample rack L to the measurement unit 51.

The pre-analysis rack holder 33 has a square shape in plan view, which width is slightly larger than the width of the sample rack L. The pre-analysis rack holder 33 is formed to be one step lower than the peripheral surface, so that the sample rack L before the analysis is mounted on the upper surface. The pre-analysis rack holder 33 is connected to the rack conveyance portion 321, so that the sample rack L is sent from the rack conveyance portion 321 by a rack sending portion 322, to be hereinafter described. A rack sensor 37 is attached near the pre-analysis rack holder 33, and a rack detection position 33*a* where the sample rack L is detected by the rack sensor 37 is arranged on the pre-analysis rack holder 33. The rack sensor 37 is an optical sensor, and includes a light emitting portion 37*a* and a light receiving portion 37*b*. The light emitting portion 37*a* is arranged on the side of the rack detection position 33*a* and the light receiving portion 37*b* is arranged on the front side of the rack detection position 33*a*. The light emitting portion 37*a* is arranged to emit light to the obliquely front side and the light receiving portion 37*b* is arranged to receive the light. Therefore, the sample rack L sent out from the rack conveyance portion 321 is positioned at the rack detection position 33*a*, wherein the light emitted from the light emitting portion 37*a* is blocked by the sample lack L and the received light level of the light receiving portion 37*a* lowers, so that the sample rack L is detected by the rack sensor 37. A rack send-in portion 33*b* is arranged projecting towards the inner side from both side surfaces of the pre-analysis rack holder 33.

When the sample rack L is detected by the rack sensor 37, the rack send-in portion 33*b* engages with the sample rack L by projecting out, and the sample rack L is moved to the back side when moved to the back side in such state (direction of approaching the rack conveyance portion 35). Such rack send-in portion 33*b* is configured to be drivable by a stepping motor 33*c* arranged on the lower side of the pre-analysis rack holder 33.

As shown in FIG. 4, the rack conveyance portion 35 can move the sample rack L moved by the pre-analysis rack holder 33 to the X direction. A sample container detection position 35*a* where the sample container is detected by the sample container sensor 38, and a sample supply position 35*c* where the sample is supplied to the measurement unit 51 of the blood cell analyzer 5 are provided on a conveyance path of the sample rack L by the rack conveyance portion 35. The rack conveyance portion 35 is configured to convey the sample rack L such that the sample is conveyed to the sample supply position 35*c* through the sample container detection position 35*a*. The sample supply position 35*c* is a position on the downstream side in the conveyance direction by one sample from the sample container detection position 35*a*, wherein when the sample is conveyed to the sample supply position 35*c* by the rack conveyance portion 35, a hand portion of the measurement unit 51 of the blood cell analyzer 5, to be hereinafter described, grips the sample container T of the relevant sample, takes out the sample container T from the sample rack L, and enables the sample to be aspirated from the sample container T, so that the sample is supplied to the measurement unit 51. After conveying the sample container to the sample supply position 35*c*, the rack conveyance portion 35 waits for the conveyance of the sample rack L during the period from the time where the supply of the sample is completed to the time where the sample container T is returned to the sample rack L.

The rack conveyance portion 35 includes two belts, a first belt 351 and a second belt 352, that are independently operable. The widths b1 and b2 in the direction of the arrow Y of the first belt 351 and the second belt 352 are the size of smaller than or equal to half of the width B in the direction of the arrow Y of the sample rack L. Such first belt 351 and second belt 352 are arranged in parallel so as not to run out from the width B of the sample rack L when the rack conveyance portion 35 conveys the sample rack L.

Figure 5:
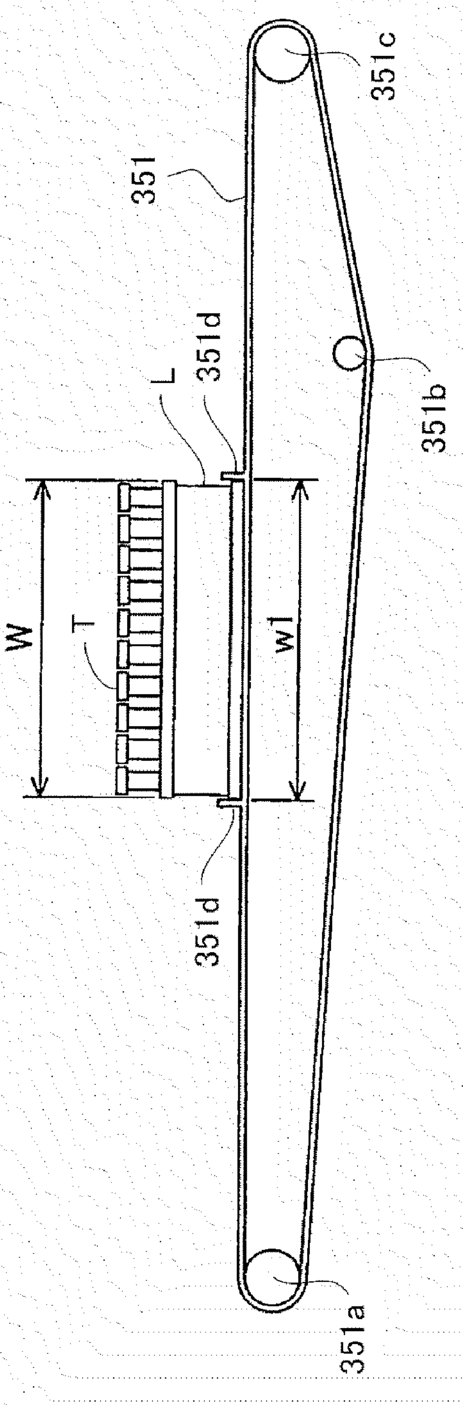
FIG. 5 is a front view showing a configuration of a first belt of the sample conveyance device.

FIG. 5 is a front view showing a configuration of the first belt 351. As shown in FIGS. 5, the first belt 351 is formed to an annular shape, wherein the first belt 351 is arranged to surround rollers 351*a* to 351*c*. Two projecting pieces 351*d* having an inner width w1 slightly (e.g., 1 mm) larger than the width W in the X direction of the sample rack L are arranged on the outer peripheral part of the first belt 351. The first belt 351 is configured to move the sample rack L in the direction of the arrow X by being moved at the outer periphery of the rollers 351*a* to 351*c* by the stepping motor 351*e* (refer FIG. 4) while holding the sample rack L on the inner side of the two projecting pieces 351*d*.

Figure 6:
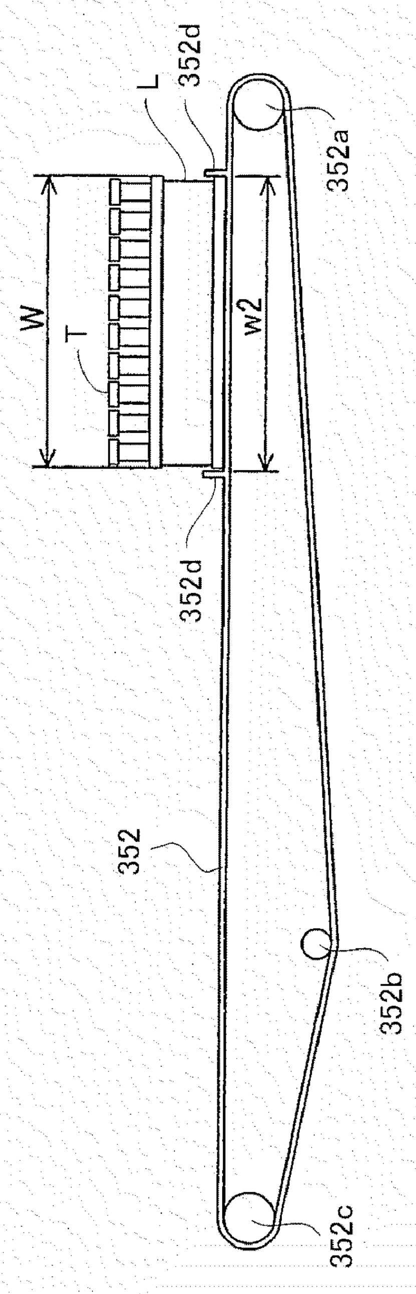
FIG. 6 is a front view showing a configuration of a second belt of the sample conveyance device.

FIG. 6 is a front view showing a configuration of the second belt 352. As shown in FIGS. 6, the second belt 352 is formed to an annular shape, wherein the second belt 352 is arranged to surround rollers 352*a* to 352*c*. Two projecting pieces 352*d* having an inner width w2 of the same extent as the inner width w1 are arranged on the outer peripheral part of the second belt 352. The second belt 352 is configured to move the sample rack L in the direction of the arrow X by being moved at the outer periphery of the rollers 352*a* to 352*c* by the stepping motor 352*e* (refer FIG. 4) while holding the sample rack L on the inner side of the two projecting pieces 352*d*. The first belt 351 and the second belt 352 are also configured to be movable the sample rack independently of each other.

The sample container sensor 38 is a contact-type sensor, and respectively includes contact piece, a light emitting element for emitting light, and a light receiving element (not shown). The sample container sensor 38 is configured such that the contact piece is bent by contacting the detecting object of the detection target, and as a result, the light emitted from the light emitting element is reflected by the contact piece and received by the light receiving element. Therefore, when the sample container T of the detection target accommodated in the sample rack L passes below the sample container sensor 38, the contact piece is bent by the sample container T, and the sample container T is detected.

The rack sending portion 39 is arranged to face the post-analysis rack holder 34, to be hereinafter described, with the rack conveyance portion 35 in between. The rack sending portion 39 is configured to move horizontally and linearly in the direction of the arrow Y by the driving force of the stepping motor 39*a*. Thus, when the sample rack L is conveyed to a position 391 (hereinafter referred to as "post-analysis rack sending position") between the post-analysis rack holder 34 and the rack sending portion 39, the rack sending portion 39 is moved to the post-analysis rack holder 34 side so that the sample rack L can be pushed and moved into the post-analysis rack holder 34. The sample rack L, which analysis is completed, is sent from the rack conveyance portion 35 to the post-analysis rack holder 34 in such manner.

The rack conveyance portion 321 extends in the direction of the arrow X in the figure, and can horizontally and linearly move the sample rack L in the direction of the arrow X. Such rack conveyance portion 321 includes an annular belt 321*a* and a stepping motor 321*b*, and is configured to rotate the belt 321*a* in the direction of the arrow X by the driving force of the stepping motor 321*b*. The sample rack L mounted on the belt 321*a* is thereby movable in the X direction. The rack sending portion 322 is arranged to face the pre-analysis rack holder 33 with the rack conveyance portion 321 in between on the front side of the pre-analysis rack holder 33. Such rack sending portion 322 is configured to horizontally and linearly move in the direction of the arrow Y by the driving force of the stepping motor 322*a*. Thus, when the sample rack L is conveyed to a position 323 (hereinafter referred to as "pre-analysis rack sending position") between the pre-analysis rack holder 33 and the rack sending portion 322, the rack sending portion 322 is moved to the pre-analysis rack holder 33 side, so that sample rack L is pushed and moved to the rack detection position 33*a* in the pre-analysis rack holder 33.

The post-analysis rack holder 34 has a square shape in plane view, which width is slightly larger than the width of the sample rack L. The post-analysis rack holder 34 is formed to be one step lower than the peripheral surface so that the sample rack L, which analysis is completed, is mounted on the upper surface thereof. The post-analysis rack holder 34 is connected to the rack conveyance portion 35, so that the sample rack L is sent from the rack conveyance portion 35 by the rack sending portion 39. A rack send-in portion 34*b* is arranged projecting towards the inner side from both side surfaces of the post-analysis rack holder 34. When the sample rack L is carried in by the rack sending portion 39, the rack send-in portion 34*b* engages with the sample rack L by projecting out, and the sample rack L is moved to the front side when moved to the front side in such state (direction of approaching the rack conveyance portion 321). Such rack send-in portion 34*b* is configured to be drivable by the stepping motor 34*c* arranged on the lower side of the post-analysis rack holder 34.

With such configuration, the conveyance mechanism 31 forms a measurement line L1, which is a conveyance line of the sample rack L through the sample supply position 35*c*, and a skip line L2, which is a conveyance line to carry out the carried-in sample rack L to the device on the downstream side without passing the sample supply position 35C.

The conveyance mechanism 31 having such configuration is controlled by the controller 32. The controller 32 is configured by CPU, ROM, RAM, and the like (not shown), and the CPU can execute the control program of the conveyance mechanism 31 stored in the ROM. The controller 32 has an Ethernet (registered trademark) interface so as to be communicably connected to the information processing unit 52 and the system control device 8 through the LAN.

According to such configuration, the sample conveyance device 3 conveys the sample rack L conveyed from the sample inserting device 2 to the pre-analysis rack sending position 323 by the rack conveyance portion 321, moves the same to the pre-analysis rack holder 33 by the rack sending portion 322, sends the sample rack L from the pre-analysis rack holder 33 to the rack conveyance portion 35, and conveys the same by the rack conveyance portion 35, so that the sample can be supplied to the measurement unit 51 of the blood cell analyzer 5. The sample rack L accommodating the sample, which aspiration is completed, is moved to the post-analysis rack sending position 391 by the rack conveyance portion 35, and sent to the post-analysis rack holder 34 by the rack sending portion 39. The sample rack L held by the post-analysis rack holder 34 is moved to the rack conveyance portion 321, and carried out to the device of the post-stage (sample conveyance device 3 or 301) by the rack conveyance portion 321. If the sample rack L accommodating the sample to be processed in the measurement unit 51 or the smear producing device 6 on the downstream side of conveyance or the sample, which analysis is completed, is accepted by the sample conveyance device 3 from the device of the pre-stage, the sample rack L is conveyed out in the direction of the arrow X by the rack conveyance portion 321, and carried out as is to the sample conveyance device 3 of the post-stage.

<Configuration of Sample Conveyance Device 301>

As shown in FIG. 1, the sample conveyance device 301 is arranged on the front side of the smear producing device 6. The sample conveyance device 301 is connected, at the right side end, to the sample conveyance device 3 positioned at the most downstream side of conveyance (left side in the figure) of the three sample conveyance devices 3, 3, 3, and is connected, at the left side end, to the sample accommodating device 4.

The sample conveyance device 301 includes a conveyor 302 and a rack slider 303. The conveyor 302 is arranged with two rack conveyance paths 302*a*, 302*b* respectively extending in the left and right direction. The rack conveyance path 302*a* proximate to the smear producing device 6 is the measurement line for conveying the sample rack L accommodating the sample to be supplied to the smear producing device 6.

The rack conveyance path 302*b* distant from the smear producing device 6 is the skip line for conveying the sample rack L not accommodating the sample to be supplied to the smear producing device 6. The conveyor 302 includes a CPU and a memory, and includes a controller (not shown) for controlling each operation mechanism.

The rack slider 303 is arranged on the right side of the conveyor 302, and allocates and inserts the sample rack L to the measurement line 302*a* and the skip line 302*b* of the conveyor 302.

<Configuration of Sample Accommodating Device 4>

The sample accommodating device 4 is configured so that a plurality of sample racks L can be mounted. The relevant sample accommodating device 4 receives the sample rack L, which is terminated with analysis and smear production, from the sample conveyance device 301, and accommodates the same.

<Configuration of Blood Cell Analyzer 5>

The blood cell analyzer 5 is a multi-item blood cell analyzer of optical flow cytometry method, and acquires the lateral scattered light intensity, the fluorescence intensity, and the like related to the blood cell contained in the blood sample, classifies the blood cell contained in the sample based on the same, counts the number of blood cells for every type, creates a scattergram in which the classified blood cells are colored by type, and displays the same. The blood cell analyzer 5 includes the measurement unit 51 for measuring the blood sample, and the information processing unit 52 for processing the measurement data output from the measurement unit 51 and displaying the analysis result of the blood sample.

As shown in FIG. 1, the blood cell analyzer 5 includes three measurement units 51, 51, 51 and one information processing unit 52. The information processing unit 52 is communicably connected to the three measurement units 51, 51, 51, and can control the operation of the three measurement units 51, 51, 51. Furthermore, the information processing unit 52 is communicably connected to the three sample conveyance devices 3, 3, 3, arranged respectively on the front side of the three measurement units 51, 51, 51.

Figure 7:
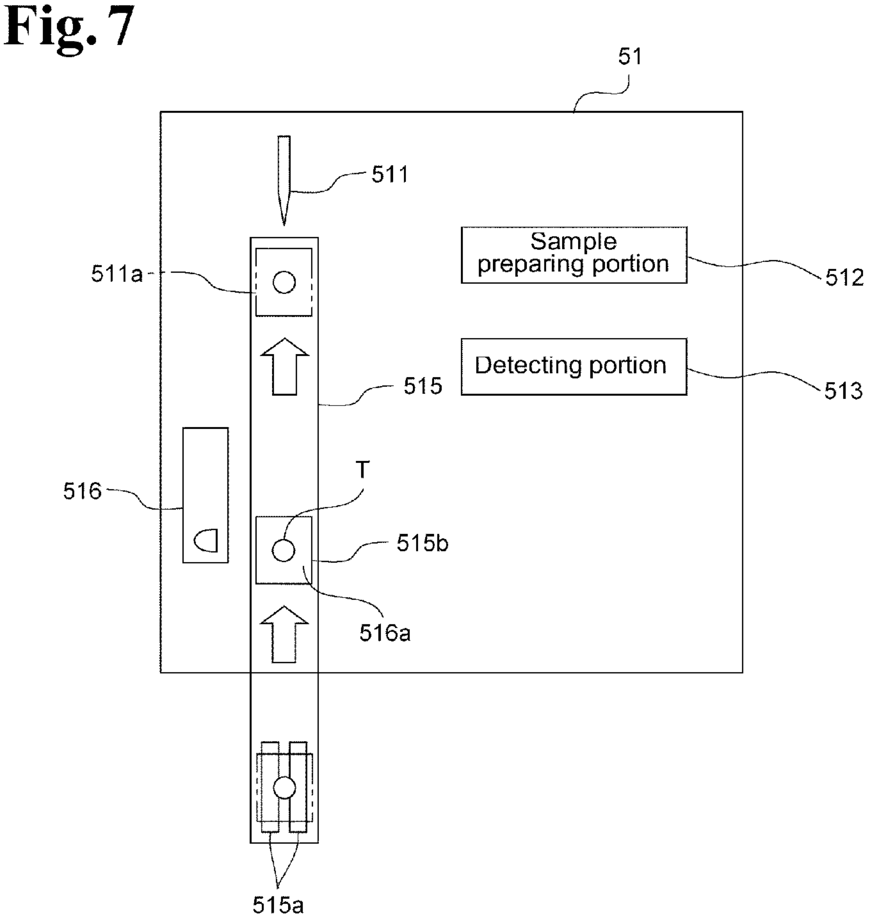
FIG. 7 is a block diagram showing a configuration of a measurement unit of a sample analyzer.

The three measurement units 51, 51, 51 have the same configuration. FIG. 7 is a block diagram showing a configuration of the measurement unit 51. As shown in FIG. 7, the measurement unit 51 includes a sample aspirating portion 511 for aspirating the blood or the sample from the sample container (blood collecting tube) T, a sample preparing portion 512 for preparing a measurement sample used in the measurement from the blood aspirated by the sample aspirating portion 511, and a detecting portion 513 for detecting the blood cell from the measurement sample prepared by the sample preparing portion 512. The measurement unit 51 further includes a take-in port (not shown) for taking in the sample container T accommodated in the sample rack L conveyed by the rack conveyance portion 35 of the sample conveyance device 3 into the measurement unit 51, and a sample container conveyance portion 515 for taking in the sample container T from the sample rack L into the measurement unit 51 and conveying the sample container T to the aspirating position by the sample aspirating portion 511.

An aspirating tube (not shown) is arranged at the distal end of the sample aspirating portion 511. The sample aspirating portion 511 is movable in the vertical direction, and is moved to the lower side so that the aspirating tube passes through the lid CP of the sample container T conveyed to the aspirating position to aspirate the blood inside.

The sample preparing portion 512 includes a plurality of reaction chambers (not shown). The sample preparing portion 512 is connected to a reagent container not shown, and can supply the reagent such as a stain reagent, a hemolytic agent, and a diluted solution to the reaction chamber. The sample preparing portion 512 is connected to the aspirating tube of the sample aspirating portion 511, and can supply the blood sample aspirated by the aspirating tube to the reaction chamber. Such sample preparing portion 512 stirs the sample and the reagent by mixture in the reaction chamber, and prepares the sample (measurement sample) for measurement by the detection portion 513.

The detecting portion 513 can perform the RBC (Red Blood Cell) detection and the PLT (Platelet) detection through the sheath flow DC detection method. In the detection of the RBC and the PLT by the sheath flow DC detection method, the measurement of the measurement sample, in which the sample and the diluted solution are mixed, is performed, wherein the information processing unit 52 performs the analyzing process on the obtained measurement data to measure the RBC and the PLT. The detecting portion 513 can perform the HGB (Hemoglobin) detection through the SLS-hemoglobin method, and is configured to be able to perform the detection of WBC (White Blood Cell), NEUT (Neutrophil Cell), LYMPH (Lymph Cell), EO (Eosinophil), BASO (Basophil) and MONO (Monocyte) through the flow cytometry method using the semiconductor laser. In the detection portion 513, detecting methods differ for the detection of the WBC not involving five classification of the white blood cell, that is the detection of the WBC not involving the detection of the NEUT, the LYMPH, the EO, the BASO and the MONO, and for the detection of the WBC involving five classification of the white blood cell. In the detection of the WBC not involving five classification of the white blood cell, the measurement of the measurement sample, in which the sample, the hemolytic agent and the diluted solution are mixed, is performed, wherein the information processing unit 52 performs the analyzing process on the obtained measurement data to measure the WBC. On the other hand, in the detection of the WBC involving five classification of the white blood cell, the measurement of the measurement sample, in which the stain reagent, the hemolytic agent and the diluted solution are mixed, is performed, wherein the information processing unit 52 performs the analyzing process on the obtained measurement data to measure the NEUT, the LYMPH, the EO, the BASO, the MONO and the WBC.

The sample container conveyance portion 515 includes a hand portion **515*a* capable of gripping the sample container T. The hand portion 515*a* includes a pair of gripping members arranged facing each other, and can approach and separate the gripping members to and from each other. The sample container T can be gripped by approaching the relevant gripping members with the sample container T in between. The sample container conveyance portion 515 can move the hand portion 515*a* in the up and down direction and in the front and back direction (Y direction), and can oscillate the hand portion 515*a*. Thus, the sample container T accommodated in the sample rack L and positioned at the sample supply position 35*c* can be gripped by the hand portion 515*a*, and the sample container T can be taken out from the sample rack L by moving the hand portion 515*a* upward in the relevant state, and the sample in the sample container T can be stirred by oscillating the hand portion 515*a***.

The sample container conveyance portion 515 includes a sample container setting portion **515*b* with a hole for inserting the sample container T. The sample container T gripped by the hand portion 515*a* described above is moved after stirring is completed, and the gripped sample container T is inserted to the hole of the sample container setting portion 515*b*. Thereafter, the sample container T is released from the hand portion 515*a* by separating the gripping members, and the sample container T is set in the sample container setting portion 515*b*. The relevant sample container setting portion 515*b* is horizontally movable in the Y direction by the power of the stepping motor (not shown). A barcode reading portion 516 is arranged inside the measurement unit 51. The sample container setting portion 515*b* is movable to a barcode reading position 516*a* near the barcode reading portion 516 and the aspirating position 511 a by the sample aspirating portion 511. When the sample container setting portion 515*b* is moved to the barcode reading position 516*a*, the set sample container T is horizontally rotated by a rotation mechanism (not shown), and the sample barcode is read by the barcode reading portion 516. Thus, even if the barcode label BL1 of the sample container T is positioned on the opposite side with respect to the barcode reading portion 516, the barcode label BL1 can be directed towards the barcode reading portion 516 by rotating the sample container T so that the sample barcode can be read by the barcode reading portion 516. When the sample container setting portion 515*b* is moved to the aspirating position, the sample is aspirated from the set sample container T by the sample aspirating portion 511**.

Figure 8:
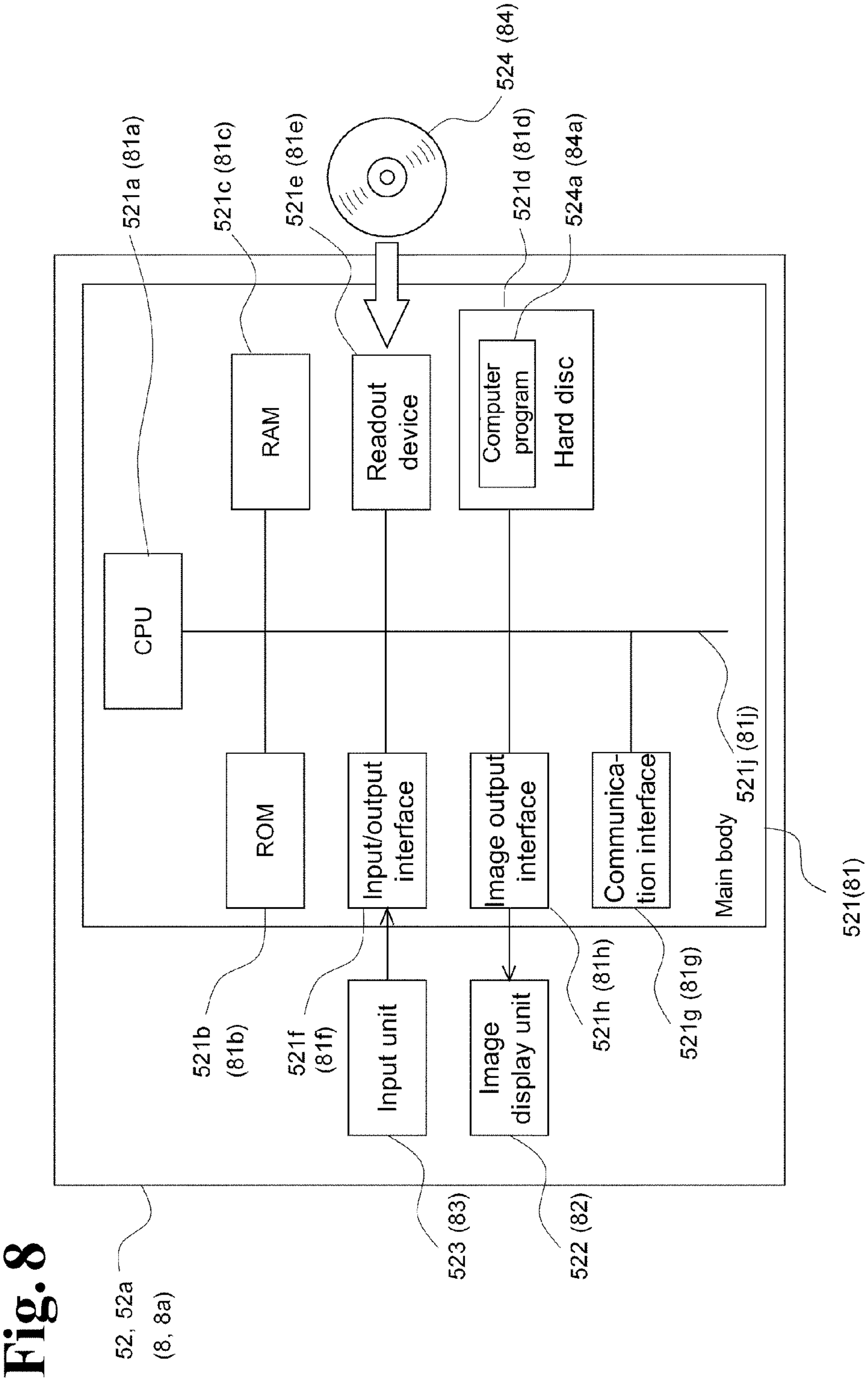
FIG. 8 is a block diagram showing a configuration of an information processing unit of the sample analyzer.

The configuration of the information processing unit 52 will now be described. The information processing unit 52 is configured by a computer. FIG. 8 is a block diagram showing the configuration of the information processing unit 52. The information processing unit 52 is realized by a computer **52*a*. As shown in FIG. 8, the computer 52*a* includes a main body 521, an image display unit 522, and an input unit 523. The main body 521 includes a CPU 521*a*, a ROM 521*b*, a RAM 521*c*, a hard disc 521*d*, a readout device 521*e*, an input/output interface 521*f*, a communication interface 521*g*, and an image output interface 521_h_, wherein the CPU 521_a_, the ROM 521_b_, the RAM 521_c_, the hard disc 521_d_, the readout device 521_e_, the input/output interface 521_f_, the communication interface 521_g_, and the image output interface 521_h_ are connected by a bus 521**_j_.

The CPU 521_a_ can execute the computer program loaded in the RAM 521_c_. The computer 52_a_ functions as the information processing unit 52 by causing the CPU 521 a to execute the computer program 524_a_ for the sample analysis and for the control of the measurement unit 51, to be hereinafter described.

The ROM 521_b_ is configured by mask ROM, PROM, EPROM, EEPROM, and the like, and is recorded with the computer program executed by the CPU 521_a_, the data used when executing the computer program, and the like.

The RAM 521_c_ is configured by SRAM, DRAM, or the like. The RAM 521_c_ is used to read out the computer program 524_a_ recorded in the hard disc 521_d_. The RAM 521_c_ is used as a work region of the CPU 521_a_ when executing the computer programs 524_a_.

The hard disc 521_d_ is installed with various computer programs to be executed by the CPU 521_a_ such as an operating system and an application program, and the data used for the execution of the computer program. The computer program 524_a_ to be hereinafter described is also installed in the hard disc 521_d_.

The readout device 521_e_ is configured by flexible disc drive, CD-ROM drive, DVD-ROM, or the like, and can read out a computer program or data recorded in a portable recording medium 524. The portable recording medium 524 stores the computer program 524_a_ for causing the computer to function as the information processing unit 52, wherein the computer 52_a_ reads out the computer program 524_a_ from the portable recording medium 524, and installs the computer program 524_a_ in the hard disc 521_d_.

The computer program 524_a_ is not limited to being provided by the portable recording medium 524, and may be provided through an electrical communication line (wired or wireless) from an external device communicably connected to the computer 52_a_ by the electrical communication line. For instance, the computer program 524_a_ may be stored in a hard disc of a server computer on the Internet, and the computer 52_a_ may access the server computer and download the computer program and store the same in the hard disc 521_d_.

The hard disc 521_d_ is installed with a multi-task operating system such as Windows (registered trademark) manufactured and sold by US Microsoft Co. In the following description, the computer program 524_a_ according to the present embodiment operates on the operating system.

The input/output interface 521_f_ is configured by serial interface such as USB, IEEE1394, or RS-232C; parallel interface such as SCSI, IDE, or IEEE1284; analog interface including D/A converter, ND converter and the like. The input/output interface 521_f_ is connected with the input unit 523 such as a keyboard and a mouse, and the user can input data to the computer 52_a_ by using the input unit 523. The input/output interface 521_f_ is connected to the three measurement units 51, 51, 51. The data can be transmitted and received with each of the three measurement units 51, 51, 51.

The communication interface 521_g_ is an Ethernet (registered trademark) interface. The communication interface 521_g_ is connected to the system control device 8 through the LAN. The computer 52_a_ can transmit and receive data with the system control device 8 connected to the LAN by using a predetermined communication protocol by the communication interface 521_g_. The communication interface 521_g_ is communicably connected to the test information managing device 9 and each sample conveyance device 3, 3, 3 through the LAN.

The image output interface 521_h_ is connected to the image display unit 522 configured by LCD, CRT, or the like, and outputs a video signal corresponding to the image data provided from the CPU 521_a_ to the image display unit 522. The image display unit 522 displays an image (screen) according to the input video signal.

<Configuration of Smear Producing Device 6>

The smear producing device 6 aspirates the blood sample, drops the blood sample on a slide glass, thinly spreads the blood sample on the slide glass, dries the blood sample, and then supplies staining fluid to the slide glass to stain the blood on the slide glass to thereby produce the smear.

Figure 9:
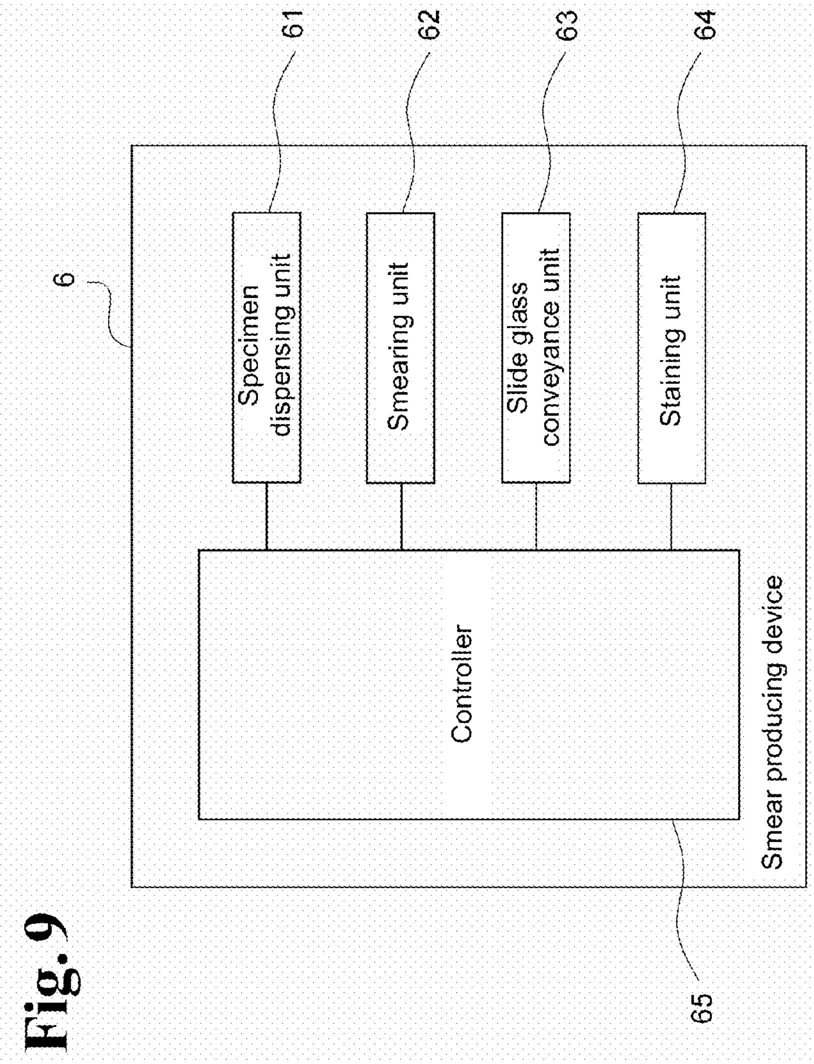
FIG. 9 is a block diagram showing a schematic configuration of a smear producing device.

FIG. 9 is a block diagram showing a schematic configuration of the smear producing device 6. As shown in FIG. 9, the smear producing device 6 includes a sample dispensing unit 61, a smearing unit 62, a slide glass conveyance unit 63, a staining unit 64, and a controller 65.

The sample dispensing unit 61 includes an aspiration tube (not shown), which the aspiration tube is pierced to the lid CP of the sample container T of the sample rack L conveyed on the measurement line 302_a_ of the sample conveyance device 301 shown in FIG. 1 to aspirate the blood sample from the sample container T. The sample dispensing unit 61 is configured to drop the aspirated blood sample on the slide glass. The smearing unit 62 is configured to smear and dry the blood sample dropped on the slide glass, and to print on the slide glass.

The slide glass conveyance unit 63 is provided to accommodate the slide glass smeared with the blood sample by the smearing unit 62 in the cassette (not shown) and further convey such cassette. The staining unit 64 supplies the staining fluid to the slide glass in the cassette conveyed to the staining position by the slide glass conveyance unit 63. The controller 65 controls the sample dispensing unit 61, the smearing unit 62, the slide glass conveyance unit 63, and the staining unit 64 according to a sample producing instruction provided from the sample conveyance device 3, and executes the smear producing operation.

<Configuration of System Control Device 8>

The system control device 8 is configured by a computer, and controls the entire sample processing system 1. The system control device 8 accepts the number of the sample rack L from the sample inserting device 2, and determines the conveying destination of the sample rack L.

The system control device 8 is realized by a computer 8_a_. As shown in FIG. 8, the computer 8_a_ includes a main body 81, an image display unit 82, and an input unit 83. The main body 81 includes a CPU 81_a_, a ROM 81_b_, a RAM 81_c_, a hard disc 81_d_, a readout device 81_e_, an input/output interface 81_f_, a communication interface 81_g_, and an image output interface 81_h_, wherein the CPU 81_a_, the ROM 81_b_, the RAM 81_c_, the hard disc 81_d_, the readout device 81_e_, the input/output interface 81_f_, the communication interface 81_g_, and the image output interface 81_h_ are connected by a bus 81_j_.

The hard disc 81_d_ is installed with various computer programs such as an operating system and an application program to be executed by the CPU 81_a_, and the data used for the execution of the computer program. The system control program 84_a_ to be hereinafter described is also installed in the hard disc 81_d_.

The hard disc 81_d_ is provided with a conveyance status database. In the conveyance status database, data showing the progress status of the process is stored for every sample rack. The conveyance status database will be described in detail hereinafter.

The readout device 81*e* is configured by flexible disc drive, CD-ROM drive, DVD-ROM, or the like, and can read out computer program or data recorded in a portable recording medium 84. The portable recording medium 84 stores the system control program 84*a* for causing the computer to function as the system control device 8, wherein the computer 8*a* reads out the system control program 84*a* from the portable recording medium 84, and installs the system control program 84*a* in the hard disc 81*d*.

The input/output interface 81*f* is configured by serial interface such as USB, IEEE1394, or RS-232C; parallel interface such as SCSI, IDE, or IEEE1284; analog interface including D/A converter, ND converter and the like. The input/output interface 81*f* is connected with the input unit 83 such as a keyboard and a mouse, and the user can input data to the computer 8*a* by using the input unit 83.

The communication interface 81*g* is an Ethernet (registered trademark) interface. The communication interface 81*g* is connected to the sample inserting device 2, the sample conveyance device 3, the sample accommodating device 4, the information processing unit 52, and the test information managing device 9 through the LAN. The computer 8*a* can transmit and receive data with each device connected to the LAN by using a predetermined communication protocol by the communication interface 81*g*.

Other configurations of the system control device 8 are similar to the configuration of the information processing unit 52, and thus the description thereof will be omitted.

<Configuration of Test Information Managing Device 9>

The test information managing device 9 is a clinical laboratory information system (LIS: Laboratory Information System). The test information managing device 9 is configured by a computer, and connected to the sample analyzer, which differs from the blood cell analyzer 5 arranged in the sample processing system 1 and the blood cell analyzer 5 arranged in other systems (for instance, a blood coagulation measurement device, an immune analyzer, a biochemical analyzer, an urine analyzer, and the like), and stores the analysis result by such sample analyzers, and display such analysis results.

Figure 10:
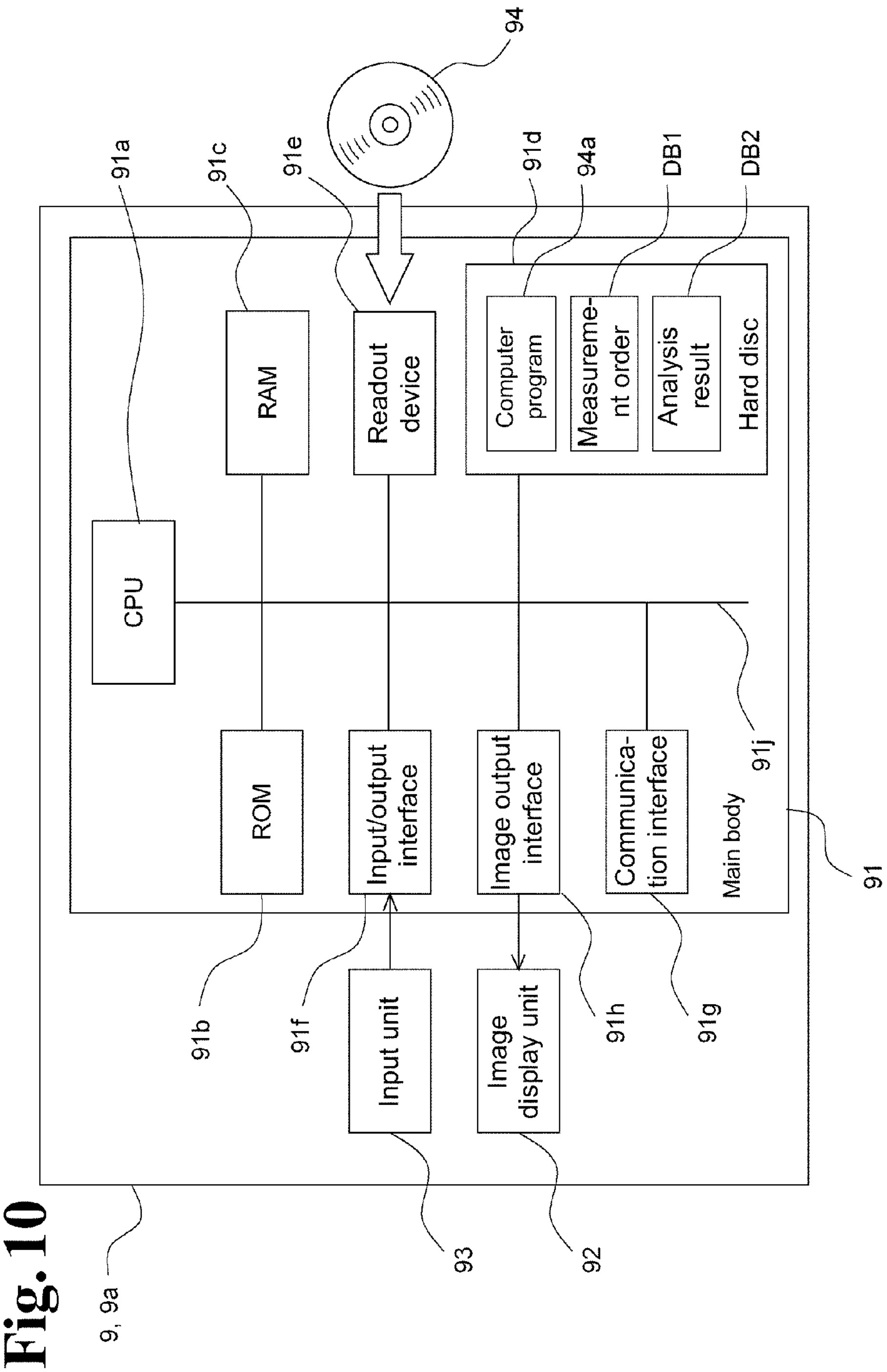
FIG. 10 is block diagram showing a configuration of a test information managing device.

FIG. 10 is a block diagram showing a configuration of the test information managing device 9. The test information managing device 9 is realized by a computer 9*a*. As shown in FIG. 10, the computer 9*a* includes a main body 91, an image display unit 92 and an input unit 93. The main body 91 includes a CPU91*a*, a ROM91*b*, a RAM91*c*, a hard disk 91*d*, a readout device 91*e*, an input/output interface 91*f*, a communication interface 91*g*, and an image output interface 91*h*, wherein the CPU 91*a*, the ROM 91*b*, the RAM 91*c*, the hard disc 91*d*, the readout device 91*e*, the input/output interface 91*f*, the communication interface 91*g*, and the image output interface 91*h* are connected by a bus 91*j*.

The hard disc 91*d* is installed with various computer programs such as an operating system and an application program to be executed by the CPU 91 a, and the data used for the execution of the computer program. The test information management program 94*a* to be hereinafter described is also installed in the hard disc 91*d*.

A measurement order database DB1 is arranged in the hard disc 91*d*. The measurement order is registered in the measurement order database DB1. The measurement order includes the information of the sample ID and the measurement item to be implemented. When receiving request data of the measurement order including the sample ID from another device, the test information managing device 9 reads out the measurement order corresponding to the sample ID from the measurement order database DB1 and transmits the same to the device of the request source.

An analysis result database DB2 is arranged in the hard disc 91*d*. The analysis result of the sample by the sample analyzer is stored in the analysis result database DB2. The analysis result includes the sample ID, a wide variety of the numerical data (RBC, PLT, HGB, WBC, NEUT, LYMPH, EO, BASO, MONO, and the like) obtained by analyzing the sample, and a distribution chart such as a scattergram and histogram. The measurement unit specifying data showing the measurement unit used in the measurement of the sample is stored in the analysis result database DB2. When receiving the analysis result from the connected sample analyzer, the test information managing device 9 registers the analysis result and the measurement unit specifying data in the analysis result database DB2. In response to the instruction given by the operator, the test information managing device 9 reads out the analysis result of the sample from the analysis result database DB2 and displays the analysis result on the image display unit 92. When the measurement order is registered in the measurement order database DB1, new record including the sample ID included in the measurement order (i.e., record not including the analysis result) is registered in the analysis result database DB2.

The readout device 91*e* is configured by flexible disc drive, CD-ROM drive, DVD-ROM, or the like, and can read out computer program or data recorded in a portable recording medium 94. The portable recording medium 94 stores the test information management program 94*a* for causing the computer to function as the test information managing device 9, wherein the computer 9*a* reads out the test information management program 94*a* from the portable recording medium 94, and installs the test information management program 94*a* in the hard disc 91*d*.

The input/output interface 91*f* is configured by serial interface such as USB, IEEE1394, or RS-232C; parallel interface such as SCSI, IDE, or IEEE1284; analog interface including D/A converter, ND converter and the like. The input/output interface 91*f* is connected with the input unit 93 such as a keyboard and a mouse, and the user can input data to the computer 9*a* by using the input unit 93.

The communication interface 91*g* is an Ethernet (registered trademark) interface. The communication interface 91*g* is connected to the sample inserting device 2, the sample conveyance device 3, the sample accommodating device 4, the information processing unit 52, and the system control device 8 through the LAN. The computer 9*a* can transmit and receive data with each device connected to the LAN by using a predetermined communication protocol by the communication interface 91*g*.

Other configurations of the test information managing device 9 are similar to the configuration of the information processing unit 52, and thus the description thereof will be omitted.

[Operation of Sample Processing System]

The operation of the sample processing system 1 according to the present embodiment will be described below.

[Sample Processing Operation]

The sample processing operation, where the sample processing system 1 conveys the sample and performs the processing of the sample (measurement or production of smear) will be described first.

<Operation of Sample Inserting Device 2>

An operator mounts the sample rack L accommodating the sample container T on the sample inserting unit 21, operates the operation panel (not shown) of the sample inserting unit 21, and gives an instruction to start the processing to the sample processing system 1. The controller 2*a* of the sample inserting device 2 accepts such instruction to start the processing, and starts to move the sample rack L. The sample rack L mounted on the sample inserting unit 21 is moved to the back side on the sample inserting unit 21, and then the sample rack L is moved to the left direction and transferred to the barcode reading unit 22.

The sample rack L introduced to the barcode reading unit 22 is moved to the left direction on the conveyance path by the controller 2*a*. The rack barcode of the sample rack L and the sample barcode of the sample container T are read by the barcode reader. The read rack ID and the sample ID are transmitted to the system control device 8 by the controller 2*a*. The sample rack is then further moved to the left direction, and the sample rack L is moved to the sample sending unit 23. The controller 2*a* moves the sample rack L accepted by the sample sending unit 23 on the sample sending unit 23. Therefore, the sample inserting device 2 transmits the carry-out request data including the rack ID to the system control device 8, and waits for the carry-out instruction data transmitted from the system control device 8. When receiving the carry-out instruction data from the system control device 8, the sample inserting device 2 carries out the sample rack L to the adjacent sample conveyance device 3, and transmits the carry-out completion data to the system control device 8.

<Operation of System Control Device 8>

The operation of the system control device 8 will be described below.

Measurement order acquiring operation of system control device 8

The system control device 8 receives the sample ID from the sample inserting device 2, inquires the measurement order to the test information managing device 9 with the sample ID as the key, and acquires the measurement order. The measurement order is the data indicating the instruction of the analysis item with which the analysis is to be performed on the sample, and includes the sample ID, the attribute information of the sample such as patient ID and patient name, and the information of the analysis item. The operation will be hereinafter described in detail below.

Figure 11:
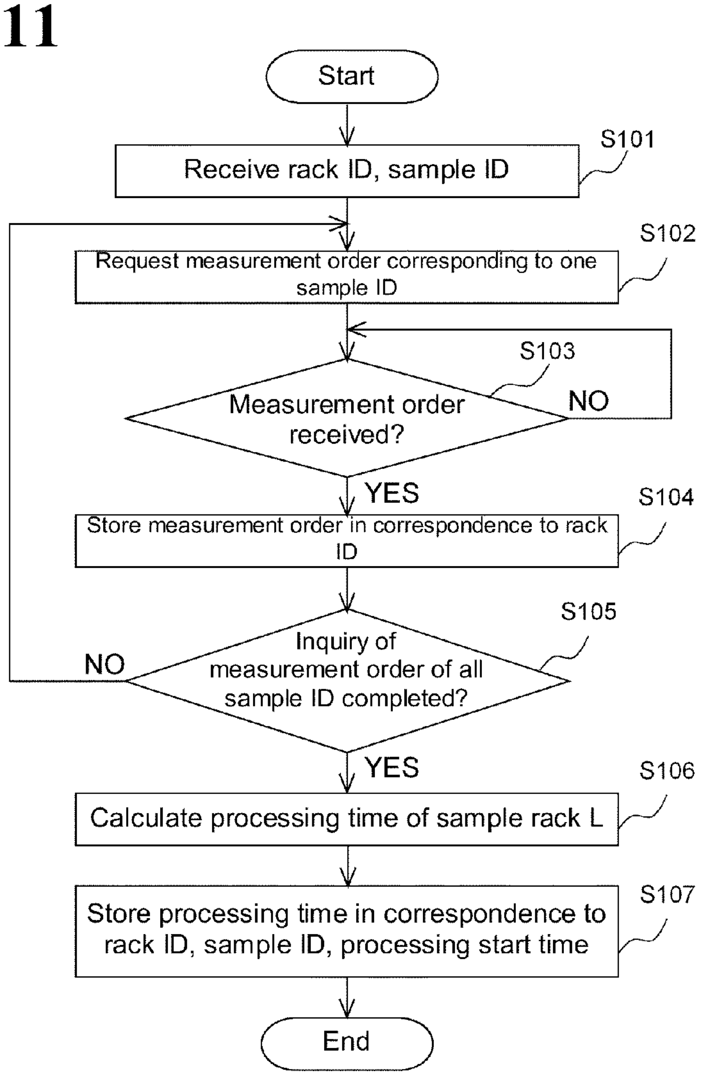
FIG. 11 is a flowchart showing the flow of the measurement order acquiring operation of the system control device.

FIG. 11 is a flowchart showing the flow of the measurement order acquiring operation of the system control device 8. As described above, the sample inserting device 2 transmits the sample ID and the rack ID read by the barcode reader to the system control device 8. The rack ID and the sample ID are received by the communication interface 81*g* of the system control device 8 (step S101). In the CPU 81*a*, the process of step S102 is called out when an event of receiving the rack ID and the sample ID occurs.

In step S102, the CPU 81*a* transmits the order request data including one of the received sample ID to the test information managing device 9, and requests the measurement order corresponding to the sample ID to the test information managing device 9 (step S102). The CPU 81*a* waits for the reception of the measurement order (NO in step S103), and stores the received measurement order in the hard disc 81*d* in correspondence to the rack ID (step S104) when the measurement order transmitted from the test information managing device 9 is received by the system control device 8 (YES in step S103).

The CPU 81 a determines whether or not the inquiry of the measurement order is completed for the sample ID corresponding to the rack ID, that is, the sample ID of all the samples accommodated in the sample rack L of the rack ID (step S105), wherein if the sample ID which measurement order is not inquired exists (NO in step S105), the CPU 81 returns the process to step S102, and requests the test information managing device 9 for the measurement order corresponding to the sample ID which measurement order is not yet inquired.

When the inquiry of the measurement order is completed for all the sample ID (YES in step S105), the CPU 81*a* calculates the time (hereinafter referred to as "processing time") necessary for the processing of all the samples accommodated in the sample rack L based on the measurement order of each sample of the sample rack L (step S106). The calculation of the processing time is calculated by adding the conveyance time of the sample rack L by the sample conveyance device 3 to the measurement time of the sample defined in advance for every measurement item. The CPU 81*a* stores the calculated processing time in the hard disc 81*d* in correspondence to the rack ID, the sample ID, and the current time (processing start time) (step S107), and terminates the process.

Conveyance instruction process from system control device 8 to sample inserting device 2

The system control device 8 receives the carry-out request data from the sample inserting device 2, determines the conveying destination of the sample rack L by using the rack ID contained in the carry-out request data, and instructs each device to convey the sample rack L to the determined conveying destination. The operation will be described in detail below.

Figure 12A:
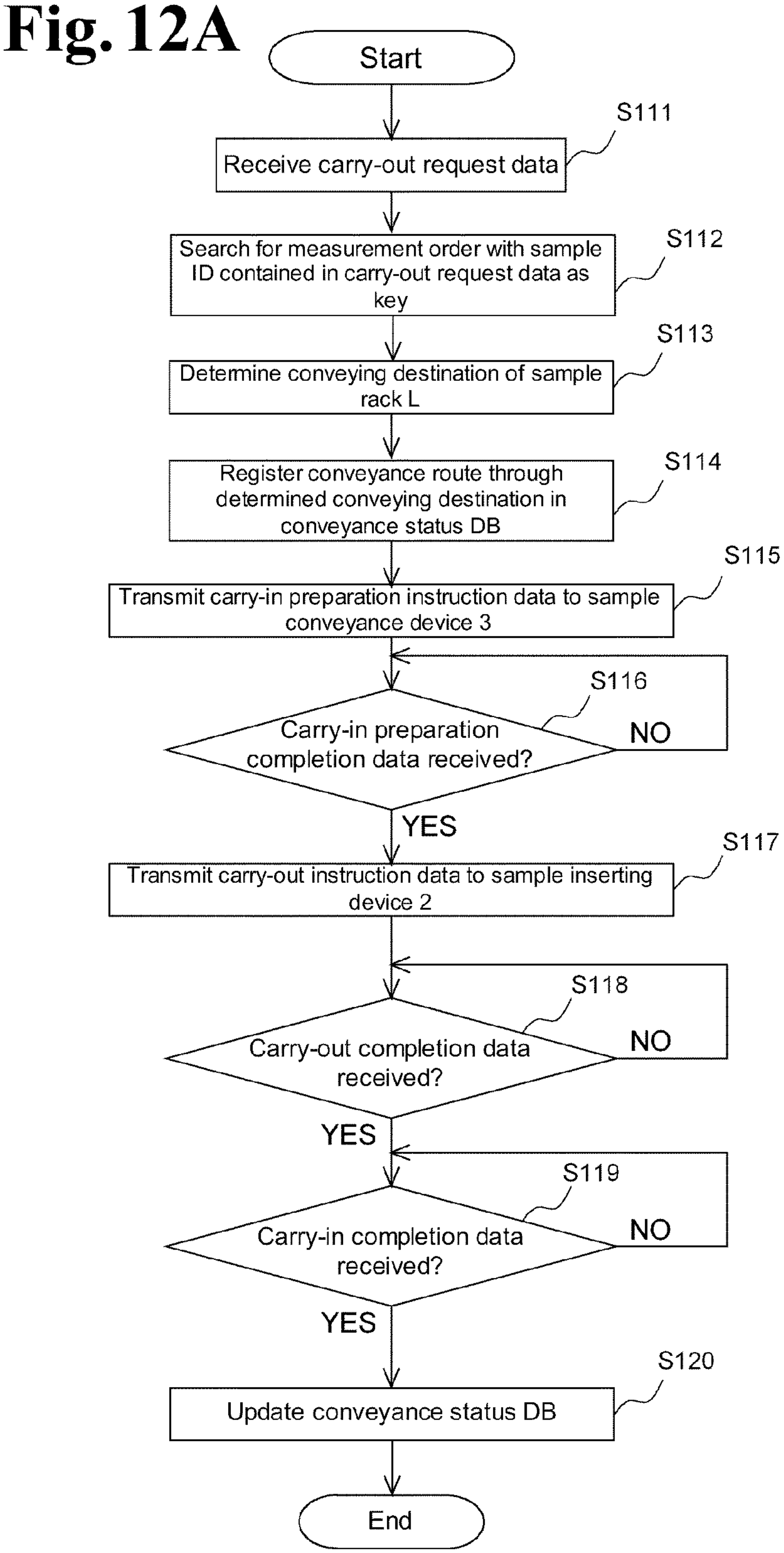
FIG. 12A is a flowchart showing a procedure of a first conveyance instruction process of the system control device.

FIG. 12A is a flowchart showing a procedure of a first conveyance instruction process of the system control device 8. In the first conveyance instruction process, the conveying destination of the sample rack L is determined, and the conveyance instruction is given to the sample conveyance device 3 arranged on the front side of the measurement unit 51 on the most upstream side in the conveyance direction. The carry-out request data transmitted from the sample inserting device 2 is received by the communication interface 81*g* of the system control device 8 (step S111). In the CPU 81*a*, the process of step S112 is called out when an event of receiving the carry-out request data occurs.

In step S112, the CPU 81*a* searches for the measurement order stored in the hard disc 81*d* with the rack ID contained in the received carry-out request data as the key (step S112). The CPU 81*a* then determines the conveying destination of the sample rack L based on the measurement item contained in each received measurement order (step S113). In this process, the measurement unit 51 where measurement is not performed at the relevant time point or the measurement unit 51 where the number of reservations of the measurement is the least, the measurement unit 51 capable of executing all the measurement items contained in the measurement order, is determined as the measurement destination.

Figure 13:
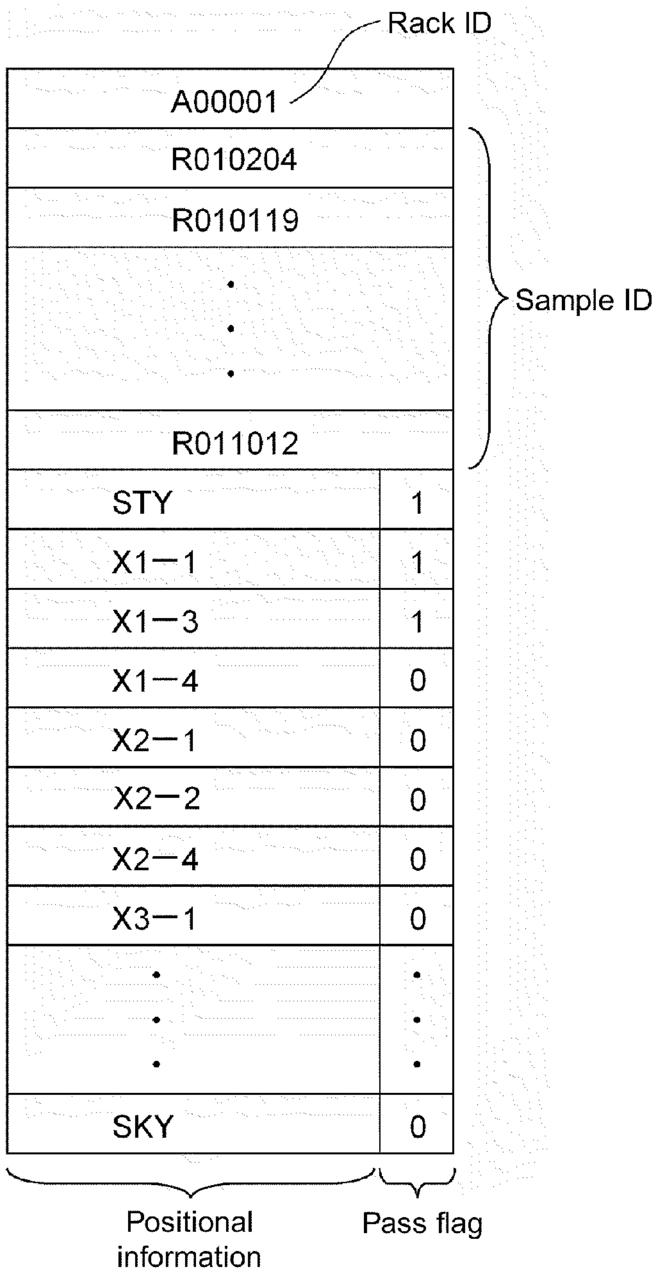
FIG. 13 is a schematic view showing a structure of a record of a conveyance status database.
Figure 14:
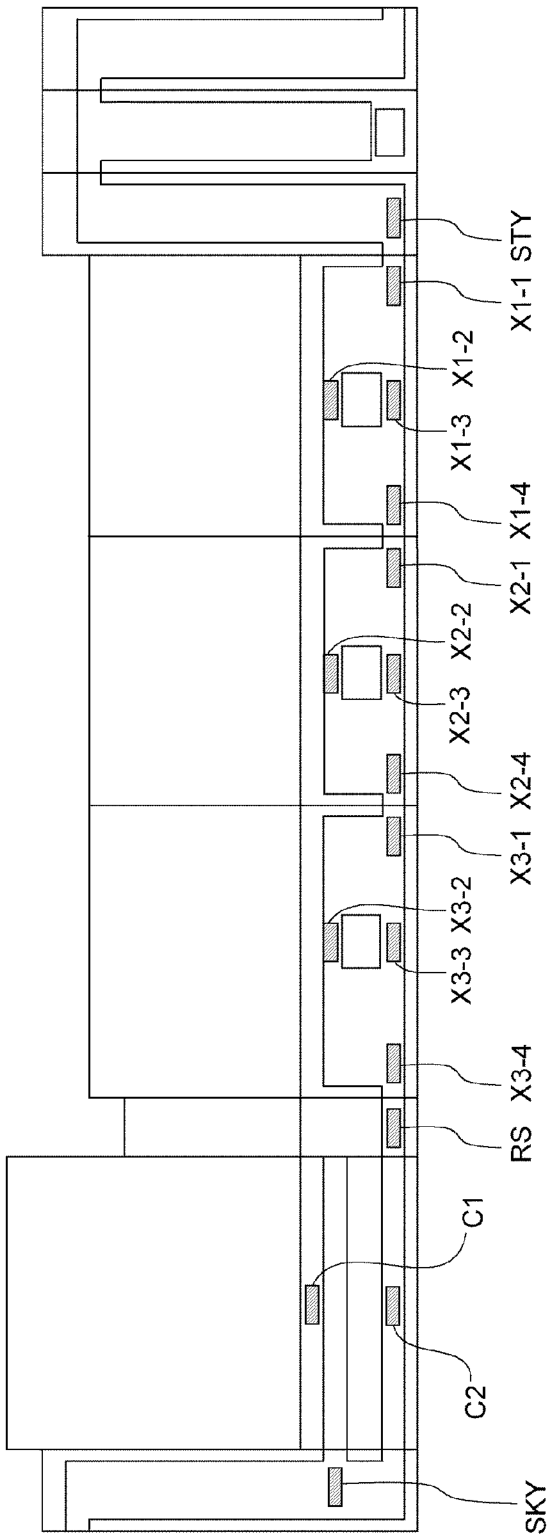
FIG. 14 is a schematic view describing the positional information defined in the sample processing system according to the embodiment.

The CPU 81*a* registers the information indicating the conveyance route through the determined conveying destination in the conveyance status database in correspondence to the rack ID of the sample rack L and the sample ID of the sample accommodated in the sample rack L (step S114). FIG. 13 is a schematic view showing a structure of a record of the conveyance status database. As shown in the figure, the record including the rack ID and the sample ID is registered in the conveyance status database. The record also includes plural positional information of the sample rack L. FIG. 14 is a schematic view describing the positional information defined in the sample processing system 1. As shown in the figure, in the present embodiment, the positional information indicating the sample sending unit 23 is the STY, the positional information indicating the rack carry-in position (position on most upstream side on rack conveyance portion 321 of sample conveyance device 3) of the first sample conveyance device 3 in the conveyance direction is X1-1, the positional information indicating the measurement line L1 of the sample conveyance device 3 is X1-2, the positional information indicating the skip line L2 of the sample conveyance device 3 is X1-3, and the positional information indicating the rack carry-out position (position on most downstream side on rack conveyance portion 321 of sample conveyance device 3) of the sample conveyance device 3 is X1-4. The positional information indicating the rack carry-in position of the second sample conveyance device 3 in the conveyance direction, the measurement line L1, the skip line L2, and the rack carry-out position are X2-1, X2-2, X2-3, and X2-4. Similarly, the positional information indicating the rack carry-in position of the third sample conveyance device 3 in the conveyance direction, the measurement line L1, the skip line L2, and the rack carry-out position are X3-1, X3-2, X3-3, and X3-4. Furthermore, the positional information indicating the rack slider 303 of the sample conveyance device 301 is RS, the positional information indicating the measurement line 302*a* and the skip line 302*b* of the conveyor 302 of the sample conveyance device 301 are C1 and C2, and the positional information indicating the sample accommodating device 4 is SKY. As shown in FIG. 13, the positional information through the conveyance route is stored in order in the record of the conveyance status database. The field of the pass flag indicating whether or not the relevant position is passed is provided in correspondence to each positional information. "0" is set to the pass flag when not passed and "1" is set when passed. When registering the new record, "1" is set to the pass flag corresponding to the positional information indicating the sample sending unit 23, and "0" is set to all other pass flags.

The conveyance status database shown in FIG. 13 shows that the content of the barcode label BL2 of the sample rack L is A00001, and that the sample rack is positioned at the positional information X1-3, that is, the skip line L2 of the first sample conveyance device 3 in the conveyance direction.

Returning to FIG. 12A, the CPU 81*a* then transmits the carry-in preparation instruction data of the sample rack L to the sample conveyance device 3 adjacent to the sample inserting device 2 (i.e., sample conveyance device 3 on rightmost side in FIG. 1) based on the determined conveying destination (step S115). The carry-in preparation instruction data contains data (hereinafter referred to as "use conveyance line instruction data") indicating the conveyance line (measurement line L1 or skip line L2) for conveying the sample rack L in such sample conveyance device 3 and the measurement order of each sample of the sample rack L. That is, if the conveying destination of the sample rack L is the measurement unit 51 on the most upstream side in the conveyance direction of the sample rack L, data indicating the measurement line L1 is set as the use conveyance line instruction data in the carry-in preparation instruction data. If other measurement units 51 are determined as the conveying destination, data indicating the skip line L2 is set as the use conveyance line instruction data in the carry-in preparation instruction data. The sample conveyance device 3 receiving the carry-in preparation instruction data executes the preparation operation (operation enabling the reception of the sample rack L) of the conveyance mechanism indicated by the use conveyance line instruction data contained in the carry-in preparation instruction data, and then transmits the carry-in preparation completion data.

The CPU 81 a waits for the carry-in preparation completion data from the sample conveyance device 3 (NO in step S116). The carry-in preparation completion data is transmitted from the sample conveyance device 3, wherein when the system control device 8 receives the carry-in preparation completion data (YES in step S116), the CPU 81*a* transmits the carry-out instruction data of the sample rack L to the sample inserting device 2 (Step S117). As described above, when receiving the carry-out instruction data, the sample inserting device 2 carries out the sample rack L to the sample conveyance device 3 and transmits the carry-out completion data.

The CPU 81*a* waits for the carry-out completion data from the sample inserting device 2 (NO in step 118). The carry-out completion data is transmitted from the sample inserting device 2, wherein when the system control device 8 receives the carry-out completion data (YES in step S118), the CPU 81*a* waits for the carry-in completion data from the sample conveyance device 3 (NO in step S119). The carry-in completion data is transmitted from the sample conveyance device 3, wherein when the system control device 8 receives the carry-in completion data (YES in step S119), the CPU 81*a* sets "1" to the pass flag corresponding to the positional information contained in the record corresponding to the rack ID of the conveyance status database, the positional information (i.e., "X1-1") indicating the rack carry-in position of the sample conveyance device 3 on the most upstream side in the conveyance direction of the sample rack L (step S120). The CPU 81*a* then terminates the process.

Figure 12B:
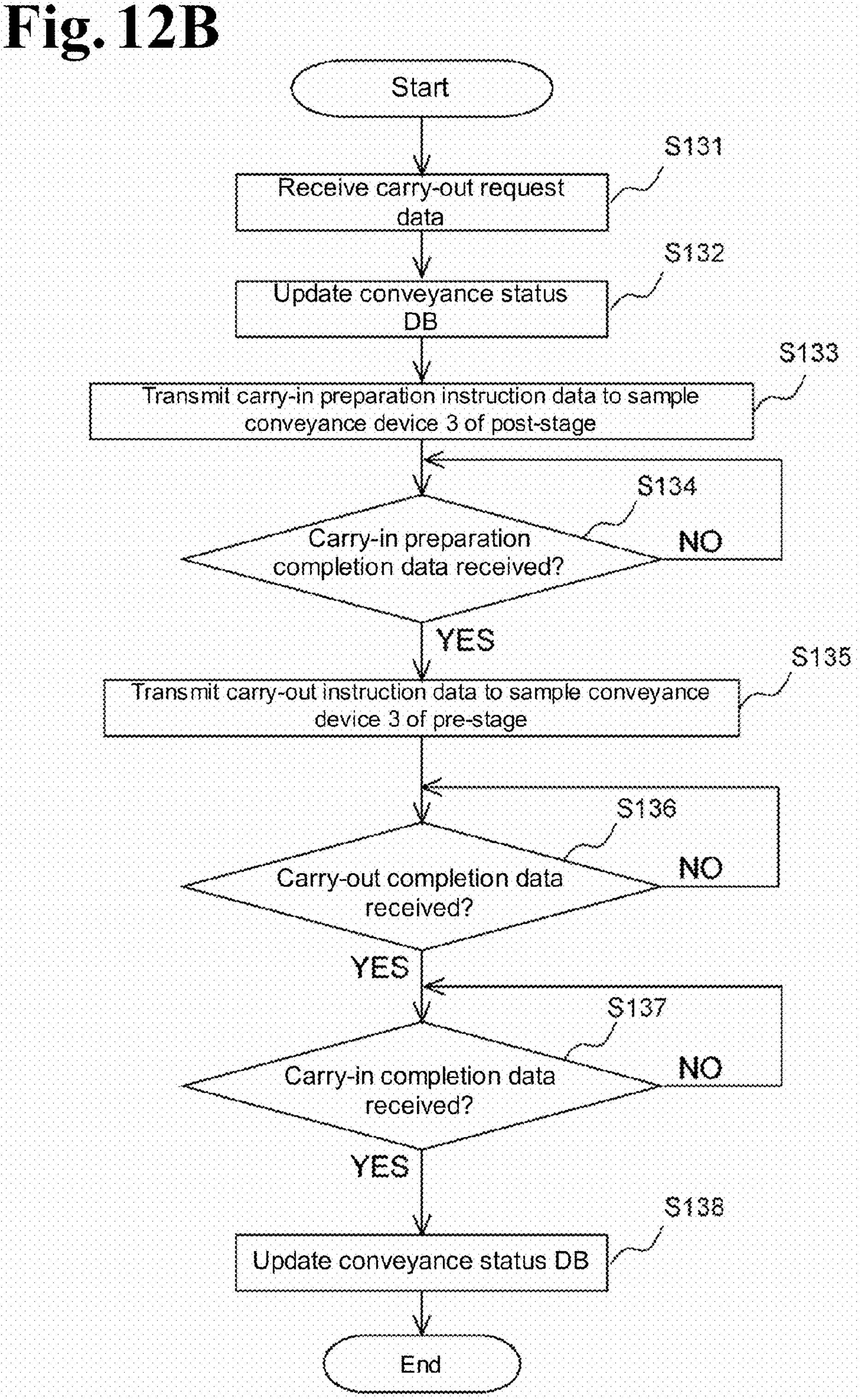
FIG. 12B is a flowchart showing a procedure of a second conveyance instruction process of the system control device.

The second conveyance instruction process transmitted from the system control device 8 to the sample conveyance device 3 will be described below. In the second conveyance instruction process, the conveyance instruction of the sample rack L is given to one of the sample conveyance devices 3. FIG. 12B is a flowchart showing a procedure of the second conveyance instruction process. When the sample rack L is conveyed by the sample conveyance device 3, and the sample rack L reaches the carry-out position for carrying out the sample rack L to the sample conveyance device 3 (or sample conveyance device 301) of the post-stage, the carry-out request data including the rack ID of the sample rack L is transmitted from the sample conveyance device 3. The carry-out request data transmitted from the sample conveyance device 3 is received by the communication interface 81*g* of the system control device 8 (step S131). In the CPU 81*a*, the process of step S132 is called out when an event of receiving the carry-out request data occurs from the sample conveyance device 3.

In step S132, the CPU 81*a* sets "1" to the pass flag corresponding to the positional information indicating the rack carry-out position of the sample conveyance device 3, the positional information being contained in the record of the conveyance status database corresponding to the rack ID contained in the received carry-out request data (step S132). The carry-out request data includes a device ID for specifying the sample conveyance device 3 of the transmission source, so that from which sample conveyance device 3 the carry-out request data is transmitted can be specified. The CPU 81 a updates the pass flag of the positional information indicating the rack carry-out position of the sample conveyance device 3 specified in the above manner (position on most downstream side on the rack conveyance portion 321 of the sample conveyance device 3) of the first, second, and third sample conveyance devices 3 in the conveyance direction in the process of step S132.

The CPU 81 a then transmits the carry-in preparation instruction data of the sample rack L based on the conveying destination determined in the conveying destination determination process to the sample conveyance device 3 of the post-stage of the relevant sample conveyance device 3 (step S133). The carry-in preparation instruction data is similar to the carry-in preparation instruction data described above, and thus the description thereof will be omitted.

The CPU 81 a waits for the carry-in preparation completion data from the sample conveyance device 3 (NO in step S134). When the carry-in preparation completion data is transmitted from the sample conveyance device 3 and the system control device 8 receives such carry-in preparation completion data (YES in step S134), the CPU 81*a* transmits the conveyance instruction data of the sample rack L to the sample conveyance device 3 of the pre-stage (carry-out side) (step S135). When receiving the conveyance instruction data, the sample conveyance device 3 of the pre-stage carries out the sample rack L to the sample conveyance device 3 of the post-stage, and transmits the carry-out completion data. The CPU 81 a waits for the carry-out completion data from the sample conveyance device 3 of the pre-stage (NO in step S136), wherein when the carry-out completion data is transmitted from the sample conveyance device 3 of the pre-stage and the system control device 8 receives such carry-out completion data (YES in step S136), the CPU 81*a* waits for the carry-in completion data from the sample conveyance device 3 of the post-stage (NO in step S137). When the carry-in completion data is transmitted from the sample conveyance device 3 of the post-stage and the system control device 8 receives such carry-in completion data (YES in step S137), the CPU 81*a* sets "1" to the pass flag corresponding to the positional information indicating the rack carry-in position of the sample conveyance device 3, the positional information being contained in the record of the conveyance status database corresponding to the rack ID (step S138). The carry-in completion data includes the device ID for specifying the sample conveyance device 3 of the transmission source, so that from which sample conveyance device 3 the carry-in completion data is transmitted can be specified. The CPU 81*a* updates the pass flag of the positional information indicating the rack carry-in position of the sample conveyance device 3 specified in the above manner of the first, second, and third sample conveyance devices 3 in the conveyance direction in the process of step S138. After the update process of the conveyance status database is completed, the CPU 81*a* terminates the process.

The system control device 8 executes the second conveyance instruction process similar to above, and updates the pass flag of the conveyance status database with respect to the sample conveyance device 301 and the sample accommodating device 4.

Conveyance status update process

While the sample rack L is being conveyed, the system control device 8 updates the record of the conveyance status database of the sample rack L. This operation will be described below.

Figure 15:
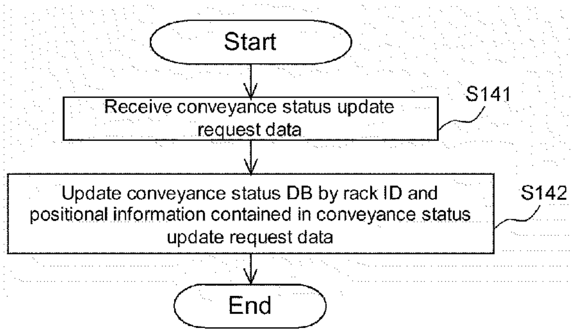
FIG. 15 is a flowchart showing a procedure of a conveyance status update process of the system control device.

FIG. 15 is a flowchart showing the procedure of the conveyance status update process of the system control device 8. As hereinafter described, the conveyance status update request data is transmitted from the sample conveyance device 3. The conveyance status update request data is received by the communication interface 81*g* of the system control device 8 (step S141). In the CPU 81*a*, the process of step S142 is called out when an event of receiving the conveyance status update request data occurs.

In step S142, the CPU 81*a* sets "1" to the pass flag corresponding to the positional information contained in the conveyance status update request data, the positional information being contained in the record of the conveyance status database corresponding to the rack ID contained in the conveyance status update request data (step S142). The conveyance status update request data includes the positional information indicating the position where the sample rack L currently exists in the sample conveyance device 3 of the transmission source. The CPU 81*a* updates the pass flag corresponding to the positional information contained in the conveyance status update request data in the process of step S142. That is, if the sample rack L is positioned on the measurement line L1 of the first sample conveyance device 3 in the conveyance direction, the conveyance status update request data includes the positional information "X1-2", wherein the pass flag corresponding to the positional information "X1-2" in the record corresponding to the rack ID of the sample rack L is updated to "1" in the process of step S142. If the sample rack L is positioned on the skip line L2 of the second sample conveyance device 3 in the conveyance direction, the conveyance status update request data includes the positional information "X2-3", wherein the pass flag corresponding to the positional information "X2-3" in the record corresponding to the rack ID of the sample rack L is updated to "1" in the process of step S142. The CPU 81*a* terminates the conveyance status update process after the process of step S142.

The conveyance status update request data is similarly transmitted from the sample conveyance device 301 and the sample accommodating device 4, wherein the system control device 8 executes the conveyance status update process similar to the above and updates the conveyance status database.

<Operation of Controller 32 of Sample Conveyance Device 3>

Figure 16A:
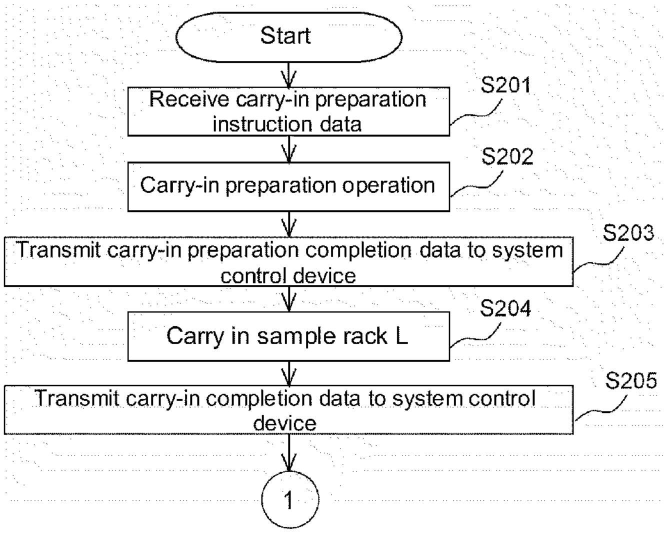
FIG. 16A and FIG. 16B are flowcharts showing a flow of a control process of the conveyance mechanism by the controller of the sample conveyance device.
Figure 16B:
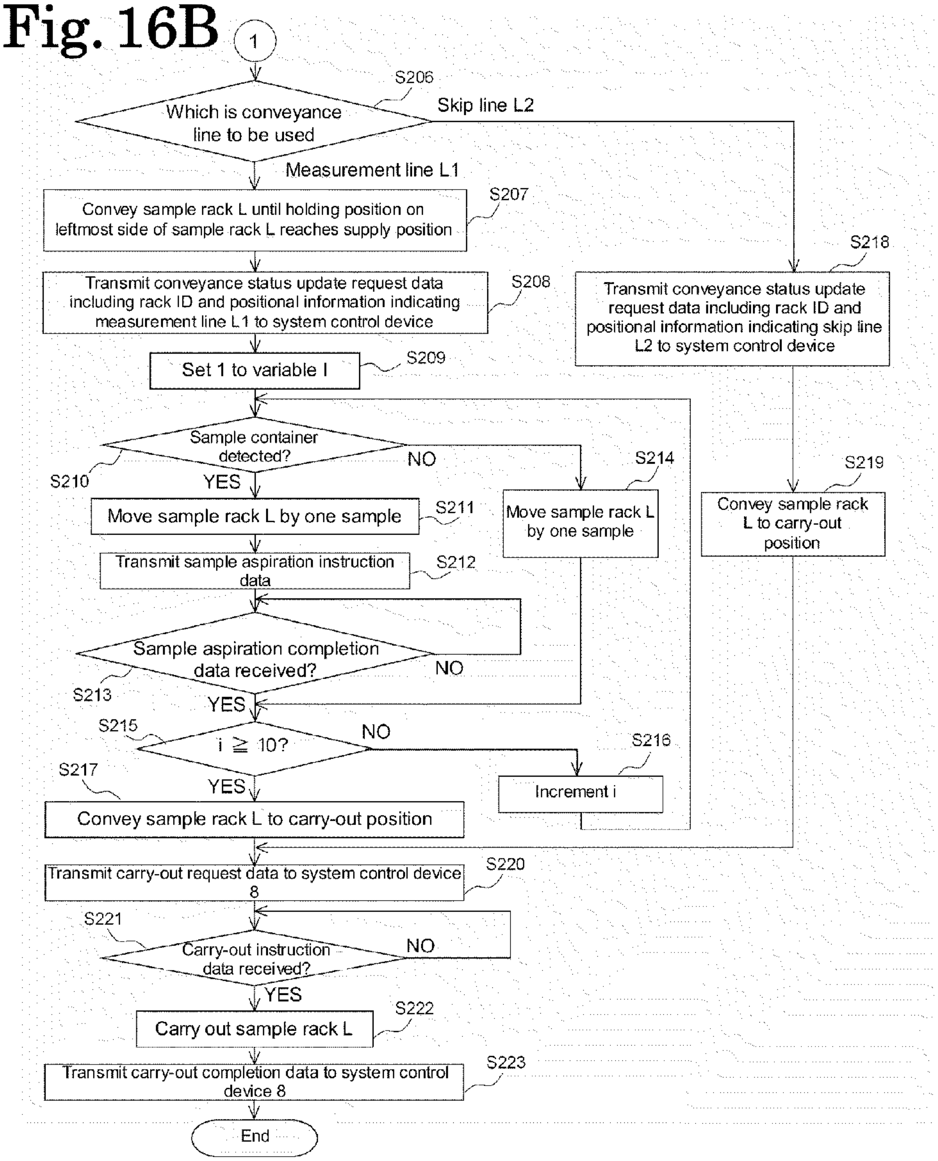

The operation of the controller 32 of the sample conveyance device 3 arranged on the front side of the measurement unit 51 will be described below. FIGS. 16A and 16B are flowcharts showing the flow of the control process of the conveyance mechanism 31 by the controller 32. The carry-in preparation instruction data transmitted from the system control device 8 is received by the controller 32 (step S201). The conveyance control program executed by the CPU of the controller 32 is an event-driven program, wherein the process of step S202 is called out when an event of receiving the carry-in preparation instruction data occurs in the controller 32.

In step S202, the controller 32 drives the belt 321*a* of the conveyance mechanism 31, for example, and executes the carry-in preparation operation (step S202). After the carry-in preparation is completed, the controller 32 transmits the carry-in preparation completion data for notifying that the carry-in preparation is completed to the system control device 8 (step S203).

In response to the transmission of the carry-in preparation completion data, the sample rack L is carried out from the device of the pre-stage, so that the sample rack L is carried in the conveyance mechanism 31 (step S204). After the carry-in of the sample rack L is completed, the controller 32 transmits the carry-in completion data notifying that the carry-in of the sample rack L is completed including the rack ID and the device ID of the sample conveyance device 3 to the system control device 8 (step S205).

The controller 32 determines whether the use conveyance line instruction data contained in the carry-in preparation instruction data indicates either the measurement line L1 or the skip line L2, that is, whether either the measurement line L1 or the skip line L2 is the conveyance line to be used (step S206). If the use conveyance line instruction data contained in the carry-in preparation instruction data indicates the measurement line L1, that is, if the measurement line L1 is the conveyance line to be used in step S206 ("measurement line L1" in step S206), the controller 32 controls the conveyance mechanism 31 and moves until the holder positioned on the leftmost side in FIG. 3 of the holders of the sample container T of the sample rack L reaches the sample container detection position (step S207). The controller 32 then transmits the rack ID and the conveyance status update request data including the positional information indicating the measurement line L1 of the sample conveyance device 3 to the system control device 8 (step S208).

The controller 32 then sets 1 to the variable i indicating the holding position of the sample container T in the sample rack L (step S209), determines whether or not the sample container T is detected at the sample container detection position by the sample container sensor 38 (step S210), wherein if the sample container T is detected (YES in step S210), moves the sample rack L in the left direction by one sample (step S211), and transmits the sample aspiration instruction data indicating the aspiration instruction of the sample to the information processing unit 52 (step S212). The sample container T detected by the sample container sensor 38 is thus positioned at the sample supply position 35*c*, and the sample is aspirated, as hereinafter described. The controller 32 waits until receiving the sample aspiration completion data (NO in step S213), and advances the process to step S215 when receiving the sample aspiration completion data (YES in step S213).

If the sample container T is not detected in step S210 (NO in step S210), the controller 32 moves the sample rack L in the left direction by one sample (step S214), and advances the process to step S215. In step S215, the controller 32 determines whether or not i is greater than or equal to 10 (step S215), increments i by one (step S216) if i is smaller than 10 (NO in step S215), and returns the process to step S210.

If i is greater than or equal to 10 in step S215 (YES in step S215), the controller 32 controls the conveyance mechanism 31 so that the sample rack L reaches the carry-out position for carrying out the sample rack L (step S217). The controller 32 then proceeds to step S220.

If the use conveyance line instruction data contained in the carry-in preparation instruction data indicates the skip line L2 in step S206, that is, if the skip line L2 is the conveyance line to be used ("skip line L2" in step S206), the controller 32 transmits the conveyance status update request data including the positional information indicating the rack ID and the skip line L2 of the sample conveyance device 3 to the system control device 8 (step S218).

The controller 32 then controls the conveyance mechanism 31 to move the sample rack L on the skip line L2 so that the sample rack L reaches the carry-out position for carrying out the sample rack L (step S219). The controller 32 then advances the process to step S220.

In step S220, the controller 32 transmits the carry-out request data including the rack ID assigned to the sample rack L and the device ID of the sample conveyance device 3 to the system control device 8 (step S220). Thereafter, the controller 32 waits for the conveyance instruction data from the system control device 8 (NO in step S221), wherein when receiving the conveyance instruction data (YES in step S221), drives the stepping motor 321*b* to carry out the sample rack L to the adjacent sample conveyance device 3 (step S222), and transmits the carry-out completion data to the system control device 8 (step S223). The controller 32 then terminates the process.

<Operation of Blood Cell Analyzer 5>

The operation of the blood cell analyzer 5 will now be described. The information processing unit 52 controls the operation of the measurement units 51, 51, 51 to measure the sample, and analyzes the measurement data obtained by the measurement.

Figure 17A:
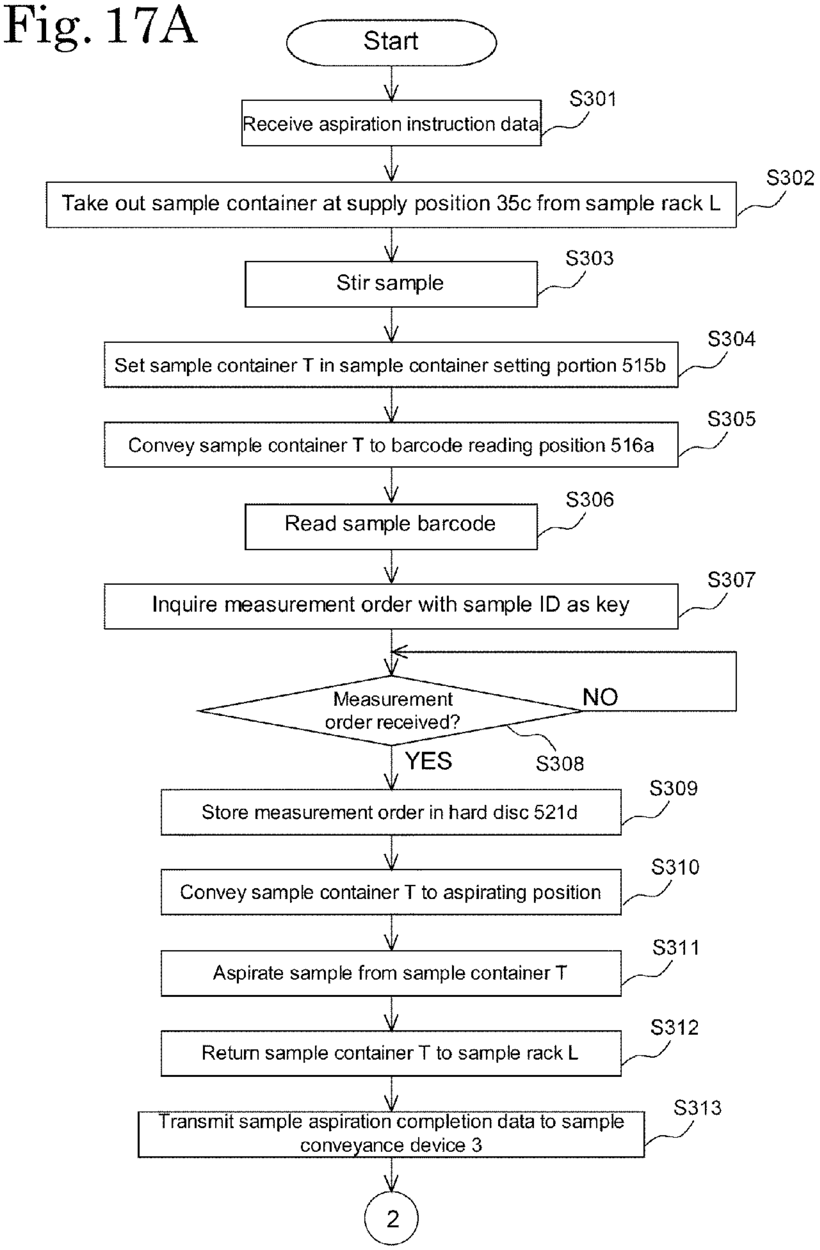
FIG. 17A and FIG. 17B are flowcharts showing a procedure of an analyzing operation of the sample by a blood cell analyzer according to the embodiment.
Figure 17B:
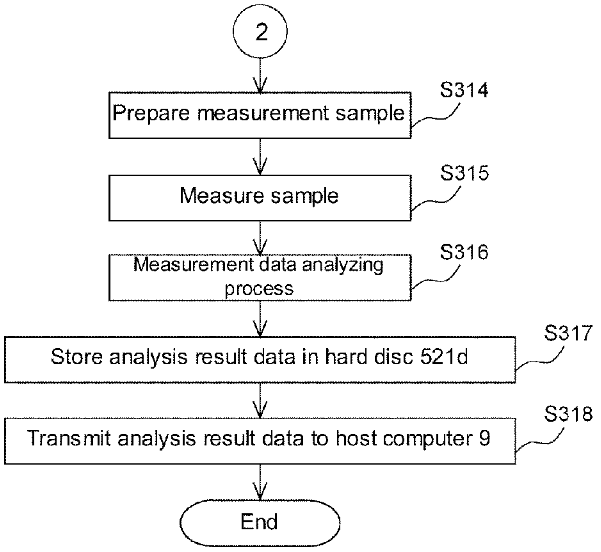

FIGS. 17A and 17B are flowcharts showing the procedure of the analyzing operation of the sample by the blood cell analyzer 5 according to the present embodiment. First, the aspiration instruction data transmitted from the controller 32 of the sample conveyance device 3 is received by the information processing unit 52 (step S301). In the CPU 521*a*, the process of step S302 is called out when an event of receiving the aspiration instruction data occurs. The aspiration instruction data includes the measurement unit ID of the measurement unit 51 to be operated.

In step S302, the CPU 521*a* controls the sample container conveyance portion 515, takes out the sample container T at the sample supply position 35*c* from the sample rack L (step S302), controls the hand portion 515*a* to oscillate the sample container T and stirs the sample inside (step S303). The CPU 521*a* controls the hand portion 515*a* to set the sample container T in the sample container setting portion 515*b* (step S304), and controls the sample container conveyance portion 515 to convey the sample container T to the barcode reading position 516*a* (step S305).

The CPU 521*a* reads the sample barcode of the sample container T by the barcode reading portion 516 and acquires the sample ID (step S306). The CPU 521*a* transmits the order request data including the sample ID to the test information managing device 9 through the communication interface 521*g* (step S307), and inquires the measurement order. Thereafter, the CPU 521*a* waits for the reception of the measurement order (NO in step S308), wherein when receiving the measurement order transmitted from the test information managing device 9 by the communication interface 521*g* of the information processing unit 52 (YES in step S308), stores the received measurement order in the hard disc 521*d* (step S309).

The CPU 521*a* controls the sample container conveyance portion 515 to convey the sample container T to the aspirating position (step S310), and controls the sample aspirating portion 511 to aspirate the sample of an amount necessary for the measurement item contained in the stored measurement order from the sample container T (step S311). After the aspiration of the sample is completed, the CPU 521*a* controls the sample container conveyance portion 515 and returns the sample container T to the sample rack L (step S312), and transmits the sample aspiration completion data to the sample conveyance device 3 conveying the sample rack L (step S313). The sample rack L is thereby conveyed by the rack conveyance portion 35.

The CPU 521*a* controls the sample preparing portion 512 to prepare the measurement sample according to the measurement item (step S314), supplies the measurement sample to the detecting portion 513 and measures the sample by the detecting portion 513 (step S315). The CPU 521*a* then acquires the measurement data output from the detecting portion 513. The CPU 521*a* executes the analyzing process of the measurement data (step S316), classifies the blood cells contained in the sample and counts the number of blood cells for every type, and creates a scattergram in which the classified blood cells are color-coded for every type. The analysis result data generated by the analyzing process of the measurement data is stored in the hard disc 521*d* with the patient information and the like contained in the measurement order (step S317), and transmitted to the test information managing device 9 (step S318). The test information managing device 9 integrates the analysis result data to the measurement order and stores the same in the hard disc. After the process of step S318 is completed, the CPU 521 terminates the process.

<Operation of Test Information Managing Device 9>

Measurement Order Providing Process

The test information managing device 9 provides the corresponding measurement order to the device of the request source when accepting the request of the measurement order from the system control device 8 or the information processing unit 52. The relevant measurement order providing process will be hereinafter described.

Figure 18:
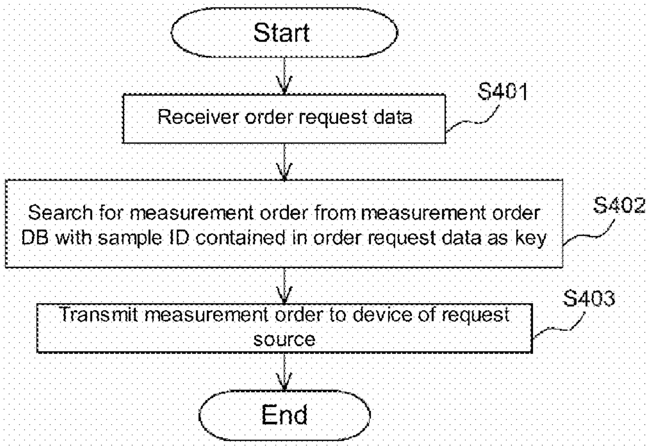
FIG. 18 is a flowchart showing a procedure of a measurement order providing process of the test information managing device.

FIG. 18 is a flowchart showing a procedure of the measurement order providing process of the test information managing device 9. The order request data is transmitted from the system control device 8 or the information processing unit 52. The order request data is received by the communication interface 91*g* of the test information managing device 9 (step S401). In the CPU 91*a*, the process of step S402 is called out when an event of receiving the order request data occurs.

In step S402, the CPU 91*a* searches for the measurement order from the measurement order database DB1 with the sample ID contained in the received order request data as a search key (step S402). The CPU 91*a* transmits the searched measurement order to the device of the request source (Step S403), and terminates the process.

Analysis result recording process

When receiving the analysis result from the information processing unit 52, the test information managing device 9 stores the relevant analysis result and the measurement unit specifying data in the analysis result database DB2. The analysis result recording process will be described below.

Figure 19:
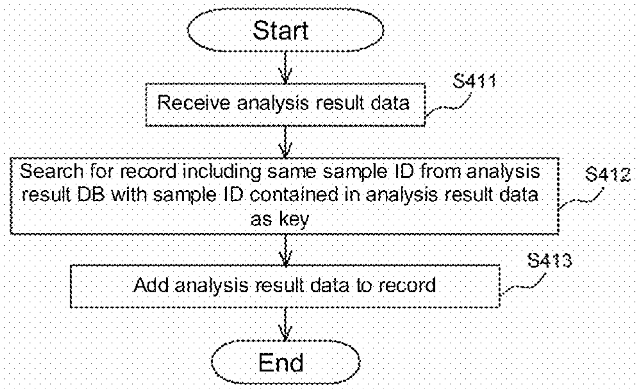
FIG. 19 is a flowchart showing a procedure of an analysis result recording process of the test information managing device.

FIG. 19 is a flowchart showing a procedure of the analysis result recording process of the test information managing device 9. The analysis result data is transmitted from the information processing unit 52. The relevant analysis result data is received by the communication interface 91*g* of the test information managing device 9 (step S411). In the CPU 91*a*, the process of step S412 is called out when an event of receiving the analysis result data occurs.

As described above, a new record including the sample ID contained in the measurement order when the measurement order is registered in the analysis result database DB2. Therefore, when the analysis result is obtained, the record of the relevant sample ID already exists in the analysis result database DB2. Therefore, the CPU 91*a* searches for the record including the same sample ID from the analysis result database DB2 with the sample ID contained in the received analysis result data as a search key (step S412). The CPU 91*a* then adds the analysis result to the searched record and updates the record (step S413). Thereafter, the CPU 91*a* terminates the process.

<Operation of Sample Conveyance Device 301>

The sample rack L sent from the sample conveyance device 3 positioned on the most downstream side in the conveyance direction is introduced to the rack slider 303. The details will be omitted, but the rack slider 303 accepts the instruction from the system control device 8, and sends the sample rack L to either the measurement line 302*a* or the skip line 302*b* of the conveyor 302. When the sample rack L is carried into the measurement line 302*a*, the controller of the conveyor 302 operates the measurement line 302*a*, and conveys the sample rack L so that the sample container T of the smear producing target is positioned at the supply position of supplying the sample to the smear producing device 6. After the supply of sample to the smear producing device 6 is completed, the measurement line 302*a* is further driven and the sample rack L is carried out to the sample accommodating device 4. When the sample rack L is carried into the skip line 302*b*, the controller of the conveyor 302 operates the skip line 302*b*, conveys the sample rack L on the skip line 302*b*, and carries out the sample rack L to the sample accommodating device 4.

When the sample rack L is carried in the rack slider 303, the sample conveyance device 301 transmits the carry-in completion data including the rack ID and the device ID to the system control device 8, and transmits the conveyance status update request data including the rack ID and the positional information (i.e., "C1") indicating the measurement line 302*a* to the system control device 8 when the sample rack L is conveyed on the measurement line 302*a* of the conveyor 302. When conveying the sample rack L on the skip line 302*b* of the conveyor 302, the conveyance status update request data including the rack ID and the positional information (i.e., "C2") indicating the skip line 302*b* is transmitted to the system control device 8. The system control device 8 that received such data updates the record of the relevant sample rack L of the conveyance status database.

<Operation of Sample Accommodating Device 4>

The sample rack L sent out from the sample conveyance device 301 is introduced to the sample accommodating device 4. The sample accommodating device 4 conveys the sample rack L on the rack mounting portion, and accommodates the same.

The sample accommodating device 4 transmits the carry-in completion data including the rack ID and the device ID to the system control device 8 when the sample conveyance device 301 carries in the sample rack L. The system control device 8 that received such carry-in completion data updates the record of the relevant sample rack L of the conveyance status database.

[Analysis Result Display Operation]

The analysis result display operation of displaying the analysis result of the sample by the sample processing system 1 with the test information managing device 9 will be described below.

<Operation of Test Information Managing Device 9>

Figure 20A:
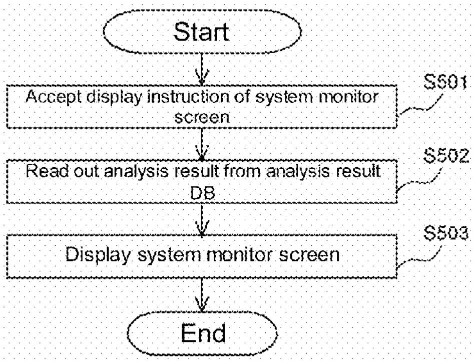
FIG. 20A is a flowchart showing a flow of a system monitor screen displaying process of the test information managing device.

FIG. 20A is a flowchart showing a flow of a system monitor screen displaying process of the test information managing device 9. The test information managing device 9 displays various screens for managing the clinical test information such as the analysis result or the measurement order on the image display unit 92. When the operator performs a predetermined input operation on the input unit 93 while the screen is displayed on the image display unit 92, the display request of the system monitor screen can be provided to the test information managing device 9. The CPU 91*a* of the test information managing device 9 accepts the display instruction of the relevant system monitor screen (step S501). In the CPU 91*a*, the process of step S502 is called out when an event of accepting the display request of the system monitor screen occurs.

In step S502, the CPU 91*a* reads out the analysis result data from the analysis result database DB2 (step S502). The CPU 91*a* then displays the system monitor screen including the read analysis result data on the image display unit 92 (step S503), and terminates the process.

Figure 21A:
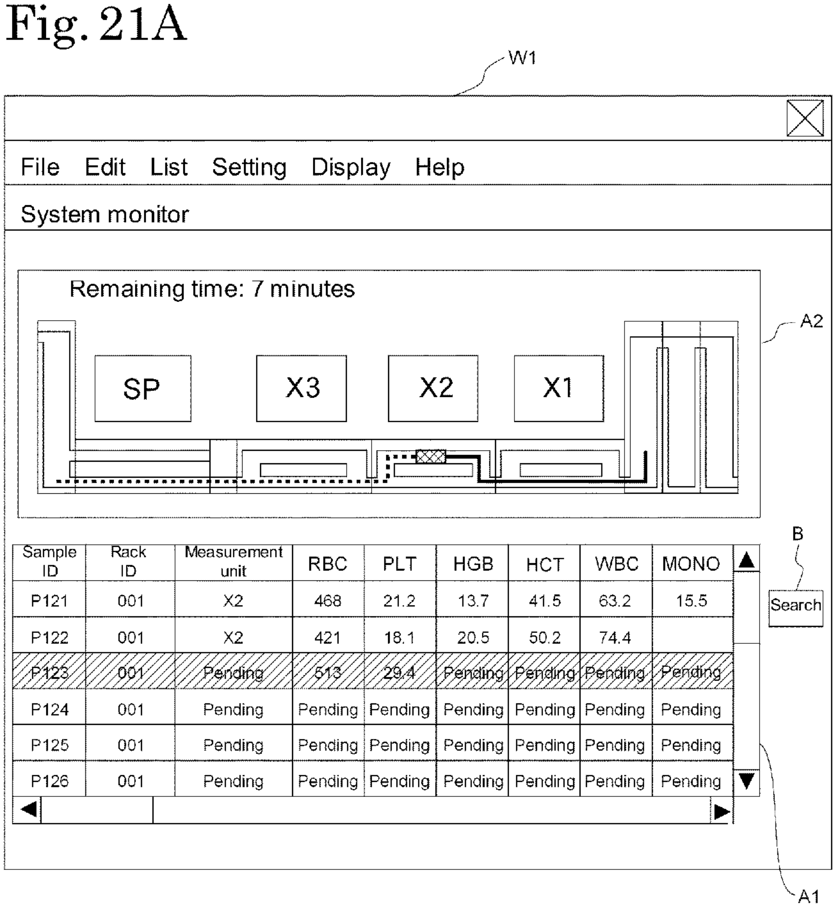
FIG. 21A is a diagram showing one example of a system monitor screen.

FIG. 21A is a view showing one example of the system monitor screen. As shown in the figure, a system monitor screen W1 includes an analysis result list display region A1 displaying the analysis result in a list, a conveyance status display region A2 including a layout chart of the sample processing system 1, and a search button B, to be hereinafter described. Furthermore, the analysis result list display region A1 includes the sample ID, the rack ID, the measurement unit used in the measurement of the sample specified by the sample ID, and the analysis result of the sample. Each row of the analysis result list display region A1 can be selected by the click operation or the like of the mouse. In the relevant analysis result list display region A1, the numerical value information of the analysis result is displayed with respect to the sample where analysis result exists in the analysis result database DB2.

With respect to the sample where analysis result does not exist in the analysis result database DB2, there is a case of waiting for the measurement result, that is, a case where measurement is executed by the measurement unit but the measurement result is not yet obtained and a case where the measurement order does not exist. In the analysis result list display region A1, the display of "Pending" indicating that the measurement result is being waited is made for the item which measurement is executed by the measurement unit but the measurement result is not yet obtained, and no display is made for the item which measurement order does not exist (blank). Furthermore, the display of "++++" is made if the numerical value of the measurement result exceeds the display range, and the display of "----" is made if the data cannot be displayed as measurement or analysis error occurred (see FIG. 24D). Thus, the operator can identify the item which analysis result exists, the item waiting for the measurement result, the item which measurement order does not exist, the item which measurement result exceeds the display range, and the non-measurable item with respect to the sample by simply checking the display of the analysis result list display region A1. Since the numerical value information of the analysis result is displayed in the analysis result list display region A1, the operator can check the analysis result. Therefore, the operator can easily find the sample and the like showing an abnormal numerical value.

The information specifying the measurement unit used in the measurement is displayed for every sample in the analysis result list display region A1. Thus, the operator can know with which measurement unit the sample is measured by simply checking the display of the analysis result list display region A1.

Figure 20B:
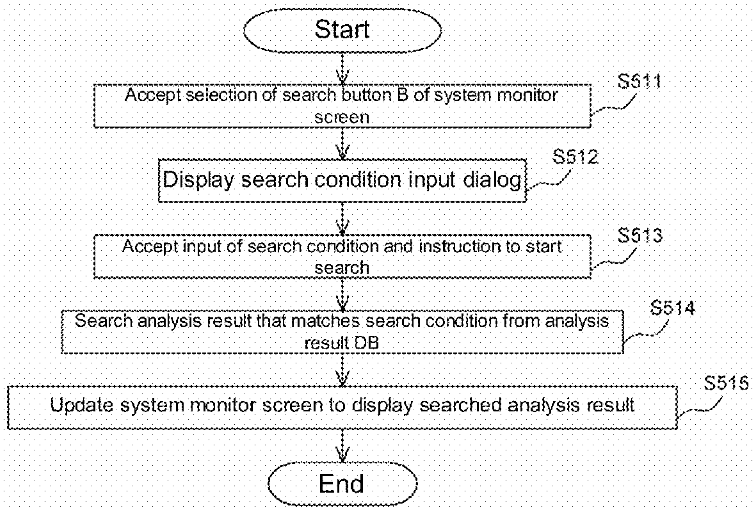
FIG. 20B is a flowchart showing a flow of an analysis result information search process of the test information managing device.

FIG. 20B is a flowchart showing a flow of an analysis result information search process of the test information managing device 9. As shown in FIG. 21A, the system monitor screen W1 includes a search button B used for the searching of the sample. The search button B can be selected through click operation or the like of the mouse by the operator. In a state the system monitor screen W1 is being displayed, the operator can select the search button B by operating the input unit 93. The CPU 91*a* of the test information managing device 9 accepts the selection of the search button B (step S511). In the CPU 91*a*, the process of the step S512 is called out when an event of accepting the selection of the search button B occurs.

Figure 21B:
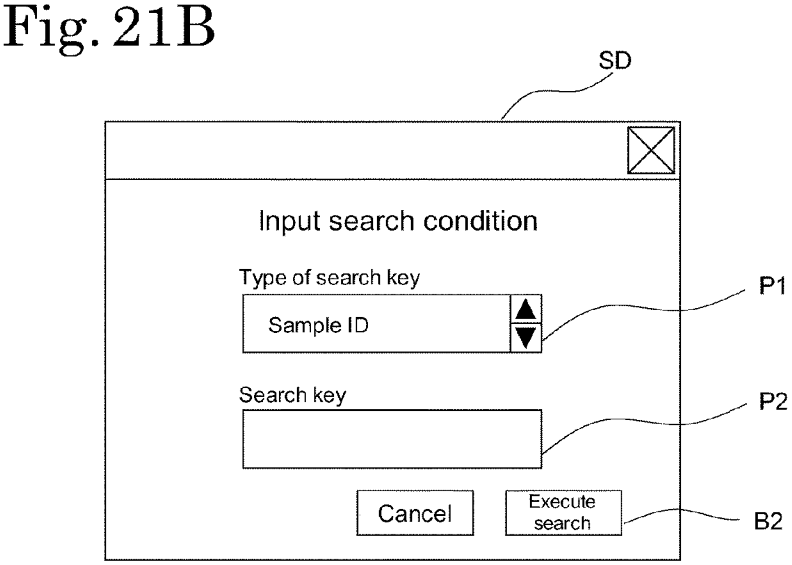
FIG. 21B is a diagram showing one example of a search condition input dialog.

In step S512, the CPU 91*a* displays a search condition input dialog (step S512). FIG. 21B is a view showing an example of the search condition input dialog. The search condition input dialog SD includes a selecting portion P1 for selecting the type of search key of sample ID, rack ID, patient name, patient ID, facility name and the like, and an input box P2 for inputting the search key. The operator selects the type of search key with the selecting portion P1 by the operation of the input unit 93, and inputs the search key to the input box P2. The search condition input dialog SD includes a search execute button B2 selectable through the click operation or the like of the mouse. When the operator selects the type of search key and inputs the search key, and then selects the search execute button B2 through the click operation or the like of the mouse, the search of the analysis result data by the input search condition (type of search key and search key) is instructed to the test information managing device 9. The CPU 91*a* of the test information managing device 9 accepts input of the search condition and the instruction to start the search (step S513). When an event of accepting the setting of the search condition and the instruction to start the search, the CPU 91*a* searches for the analysis result that matches the search condition from the analysis result database DB2 (step S514). The CPU 91*a* then updates the system monitor screen so as to display the searched analysis result data (step S515) and terminates the process. The analysis result of the relevant sample thus can be displayed on the system monitor screen when a sample which analysis result and the conveyance status the operator desires to check exists. The conveyance status of the sample can be displayed by having the operator select such sample.

Figure 20C:
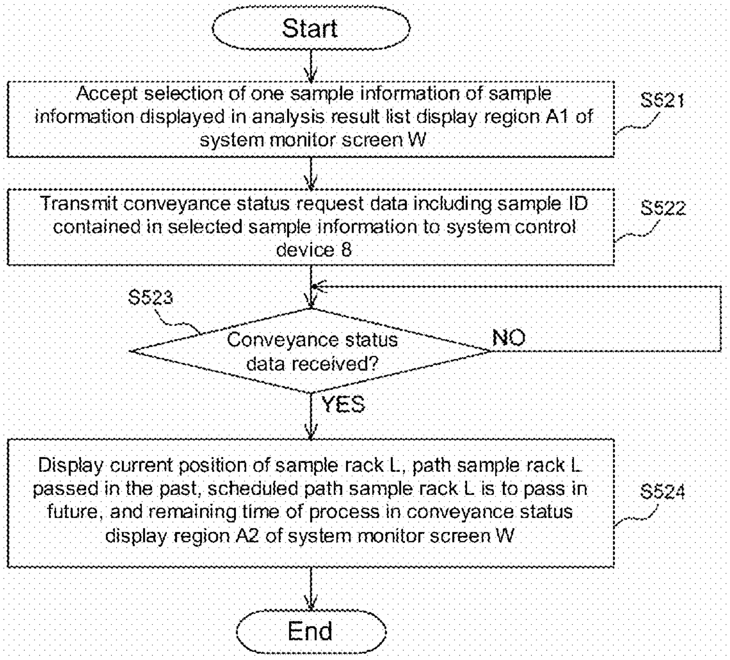
FIG. 20C is a flowchart showing a flow of a sample conveyance status displaying process of the test information managing device.

FIG. 20C is a flowchart showing a flow of a sample conveyance status displaying process of the test information managing device 9. When the operator operates the input unit 93 while the system monitor screen W1 is being displayed, an arbitrary sample displayed in the analysis result list display region A1 can be selected. The CPU 91*a* of the test information managing device 9 accepts the selection of the relevant sample (step S521). In the CPU 91*a*, the process of step S522 is called out when an event of accepting the selection of the sample occurs.

In step S522, the CPU 91*a* transmits the conveyance status request data including the sample ID contained in the selected sample to the system control device 8 (step S522). Thereafter, the CPU 91*a* waits for the reception of the conveyance status data indicating the conveyance status of the sample (NO in step S523). When the test information managing device 9 receives the conveyance status data (YES in step S523), the CPU 91 a displays the current position of the sample rack L, the path the sample rack L passed in the past, the scheduled path the sample rack L is to pass in the future, and the remaining time of the process in the conveyance status display region A2 of the system monitor screen W1 based on the received conveyance status data (step S524), and terminates the process.

The conveyance status data includes the rack ID, each positional information and pass flag contained in the record corresponding to the rack ID in the conveyance status database, and the information of the remaining time of the process. For instance, the conveyance status data necessary for the display of the conveyance status display region A2 shown in FIG. 21A includes "STY, X1-1, X1-3, X1-4, X2-1, X2-2, X2-4, X3-1, X3-3, X3-4, RS, C2, SKY" as positional information. The conveyance status data has "1" set to the pass flag corresponding to STY to X2-2, and "0" set to the pass flag corresponding to X2-4 to SKY.

As shown in FIG. 21A, in the conveyance status display region A2, the path the sample rack L already passed is displayed with a solid line, and the path the sample rack L has not passed is displayed with a broken line. Thus, the CPU 91*a* displays the passed path and the non-passed path in a distinguishable manner. The operator thus can grasp the content of the process performed up to the relevant point and the content of the process scheduled to be performed in addition to the current position of the sample rack L. The remaining time until the sample rack L is accommodated in the sample accommodating device 4 is displayed in the conveyance status display region A2. The operator thus can grasp the remaining time until the process is completed.

When the sample which process is completed is selected, the conveyance path of the sample rack L for accommodating such sample is all passed paths. Therefore, the conveyance paths of the sample rack L are all displayed with a solid line in the conveyance status display region A2 in this case. The operator can grasp the history of the process of the sample such as which conveyance path the relevant sample passed and with which measurement unit 51 the measurement was performed by checking the conveyance path the sample passed. In such case, the remaining time is displayed as "0".

The operator can easily understand that the process of the relevant sample is completed by looking at the display of the remaining time.

<Operation of System Control Device 8>

Figure 22:
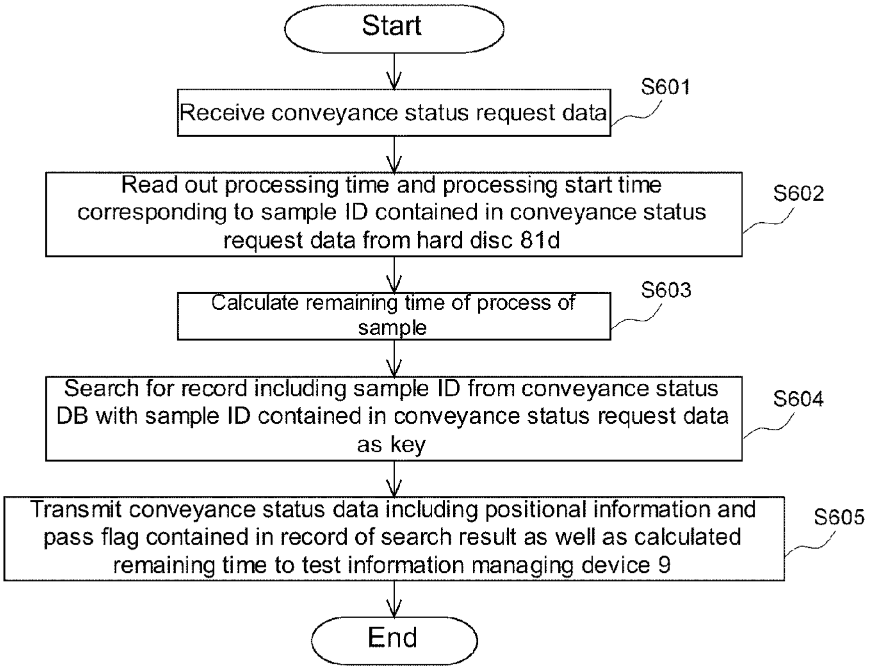
FIG. 22 is a flowchart showing a flow of a conveyance status notification process of the system control device.

The operation of the system control device 8 in the analysis result display operation will now be described. FIG. 22 is a flowchart showing a flow of a conveyance status notification process of the system control device 8. As described above, the test information managing device 9 transmits the conveyance status request data including the sample ID to the system control device 8. Such conveyance status request data is received by the communication interface 81 g of the system control device 8 (step S601). In the CPU 81*a*, the process of step S602 is called out when an event of receiving the conveyance status request data occurs.

In step S602, the CPU 81*a* reads out the processing time and the processing start time corresponding to the sample ID contained in the conveyance status request data from the hard disc 81*d* (step S602). The CPU 81*a* then calculates the remaining time of the process of the sample by subtracting the time (elapsed time) elapsed from the processing start time to the current time from the processing time (step S603). In this process, the remaining time is "0" when the remaining time becomes smaller than or equal to 0 (i.e., when processing of the sample is completed).

The CPU 81*a* then searches for the record including the sample ID from the conveyance status database with the sample ID contained in the conveyance status request data as a key (step S604), and transmits the conveyance status data including the positional information and the pass flag contained in the record obtained through search as well as the calculated remaining time to the test information managing device 9 (step S605). Thereafter, the CPU 81*a* terminates the process.

<Transition of Display Screen of Test Information Managing Device 9>

Figure 23:
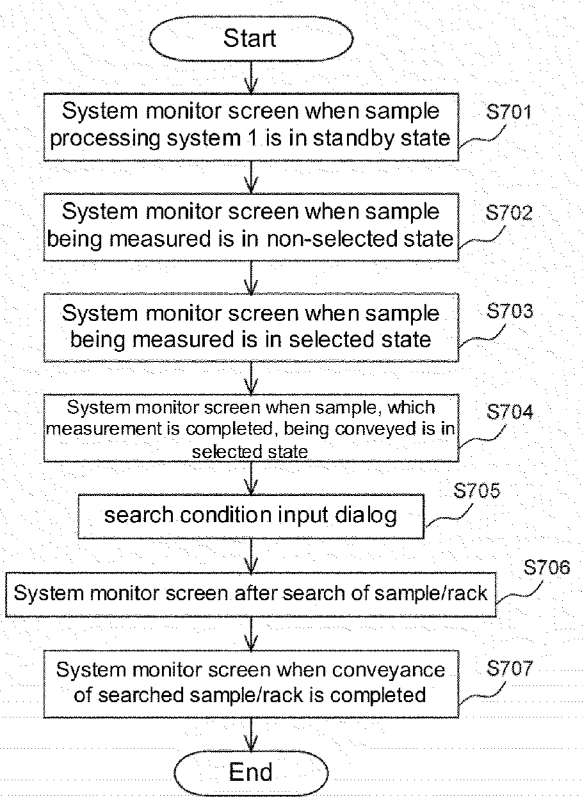
FIG. 23 is a flowchart showing one example of a transition of a displaying screen of the test information managing device.

The transition of the display screen of the test information managing device 9 will now be described. FIG. 23 is a flowchart showing an example of the transition of the display screen of the test information managing device 9. Immediately after the sample processing system 1 is activated, the sample processing system 1 is in a standby state in which the sample is not measured, the sample rack L is not conveyed, and the measurement preparation of the sample and the conveyance preparation of the sample rack are completed.

Figure 24A:
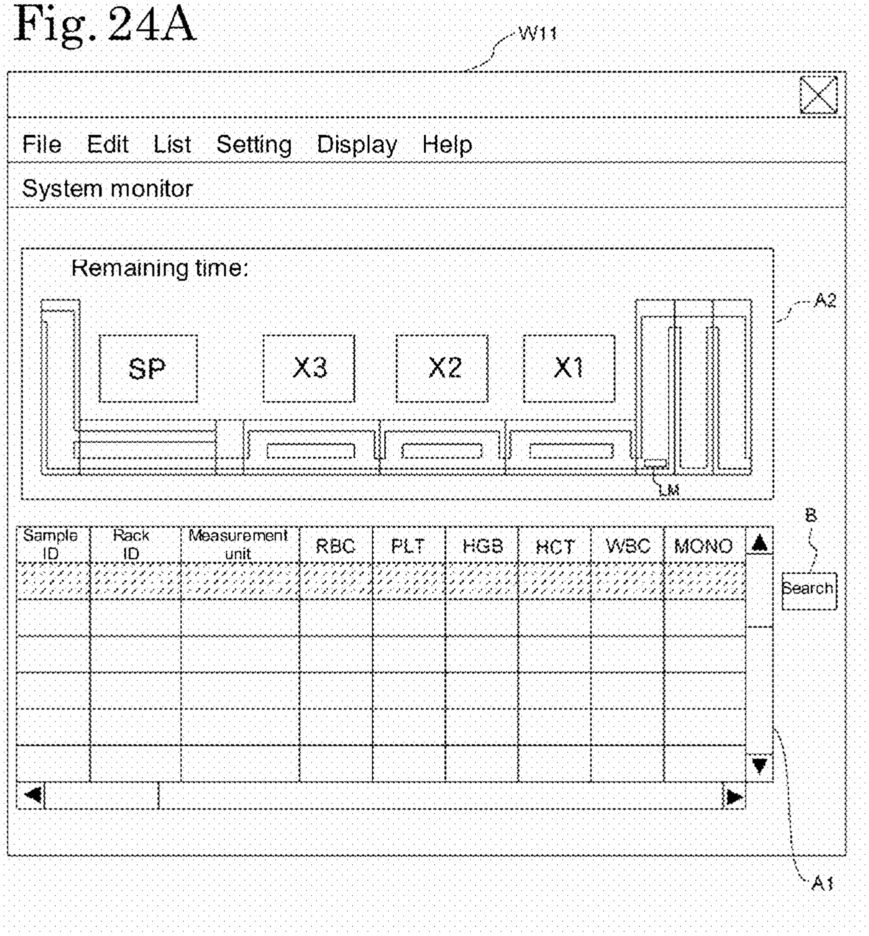
FIG. 24A is a diagram showing one example of the system monitor screen when the sample processing system is in a standby state.

FIG. 24A is a view showing a system monitor screen of when the sample processing system 1 is in standby state. When the sample processing system 1 is in standby state, the system monitor screen as shown in FIG. 24A is displayed (step S701). The system monitor screen W11 shown in FIG. 24A is a state in which the sample rack L is inserted to the sample inserting device 2 and the record of the sample rack L is registered in the conveyance status database. The system monitor screen W11 in this case shows an image (hereinafter referred to as "rack mark") LM of a square frame showing the sample rack L only at the position (position of STY in FIG. 14) of the sample inserting device 2 in the conveyance status display region A2. The rack mark LM is not selected by the user, and the inside of the frame is white of non-selected color.

In such state, since not even one sample rack L is conveyed by the sample conveyance devices 3, 301 of the sample processing system and the analysis result data of the sample accommodated in the sample rack L inserted to the sample inserting device 2 is not registered in the analysis result database DB2, not even one numerical value data of the sample ID, the rack ID, and the analysis result is displayed in the analysis result list display region A1. The uppermost line in the analysis result list display region A1 is not in a selected state but in a temporarily selected state, and such line is displayed with a temporarily selected color of light blue. Furthermore, the remaining time is not displayed in the system monitor screen W11 since the remaining time is not yet calculated.

Figure 24B:
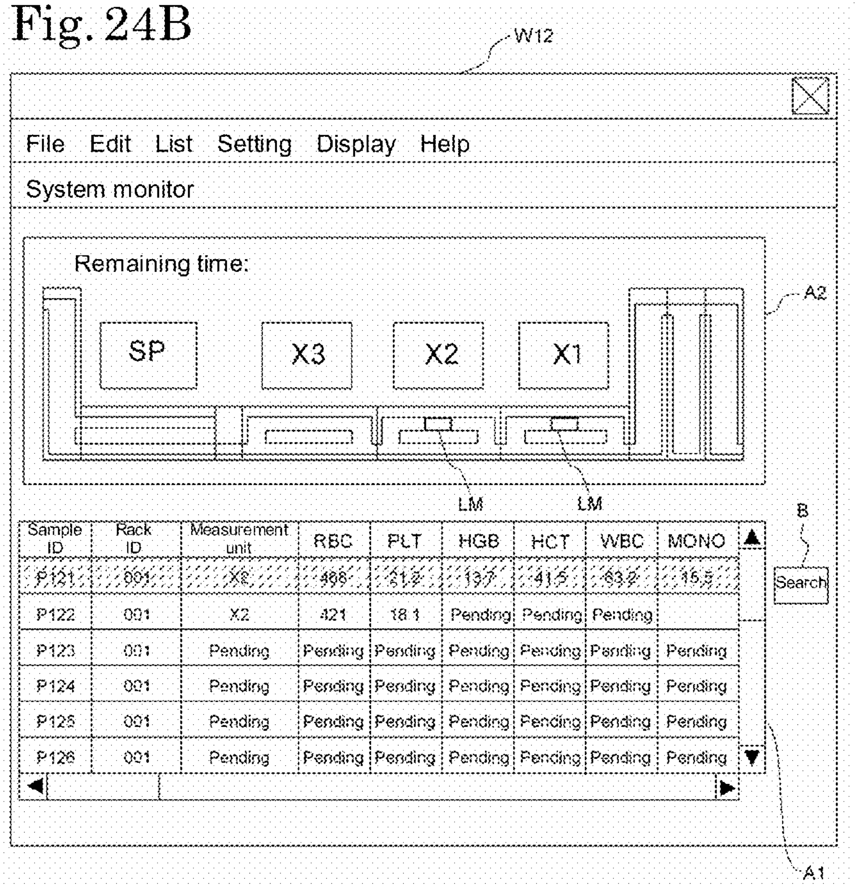
FIG. 24B is a diagram showing one example of the system monitor screen when the sample is being measured.

When the measurement of the sample starts from the standby state, the sample rack L is conveyed by the sample conveyance device 3, and the sample is measured by the measurement unit 51. The screen display changes to the system monitor screen of the case where the sample being measured is in non-selected state (step S702). FIG. 24B is a view showing a system monitor screen of the case where the sample is being measured. The system monitor screen W12 shown in FIG. 24B shows a state in which the samples of two sample racks L are measured by the measurement units 51, 51, and such sample rack L and the sample are not selected. In the system monitor screen W12 of this case, the rack mark LM is drawn at the measurement line L1 (position of X1-2 in FIG. 14) of the first sample conveyance device 3 in the conveyance direction of the conveyance status display region A2 and the measurement line L1 (position of X2-2 in FIG. 14) of the second sample conveyance device 3 in the conveyance direction. The rack mark LM in this case is not selected by the user, and thus the inside of the frame is white or the non-selected color.

The analysis result list display region A1 of the system monitor screen W12 is displayed with the numerical value data of the sample ID, the rack ID, and the analysis result related to the sample rack L conveyed by the sample conveyance device 3. The rack ID of the sample rack L being conveyed on the measurement line L1 of the second sample conveyance device 3 in the conveyance direction is "001", and such rack ID is displayed in the analysis result list display region A1. In the system monitor screen W12, the information of any of the samples displayed in the analysis result list display region A1 is not selected, and the information related to the sample (sample having sample ID "P121") displayed at the uppermost part of the analysis result list display region A1 is in the temporarily selected state, wherein such line is displayed with the temporarily selected color of light blue. Since none of the lines (sample) is selected, the remaining time is not displayed in the system monitor screen W12.

In such analysis result list display region A1, the numerical value is displayed in the corresponding cell every time the numerical value data of the measurement result is obtained. In the numerical value data of the measurement result obtained by the analyzing process of the information processing unit 52, the obtained time differs depending on the measurement item. That is, even the numerical value of the RBC and the PLT measured by the same measurement method are simultaneously obtained for the measurement result of one sample "P122", but the numerical value data of the HGB measured through a different measurement method is acquired after the RBC and the PLT. Therefore, in the screen shown in FIG. 24B, the numerical value data of the RBC and the PLT are obtained for the sample "P122" and are displayed, but the display of "Pending" indicating wait for the measurement result is displayed in the corresponding cell since the numerical value data of the HGB, HCT, and the WBC of the relevant sample are not obtained at this time point.

The numerical value data of the sample ID, the rack ID, and the analysis result related to another sample rack L (sample rack L being conveyed on the measurement line L1 of the first sample conveyance device 3 in the conveyance direction) are not displayed in the analysis result list display region A1, but the display of the analysis result list display region A1 can be scrolled by having the user operate the scroll bar arranged at the right side of the analysis result list display region A1, whereby the information related to the other sample rack L can be displayed.

Figure 24C:
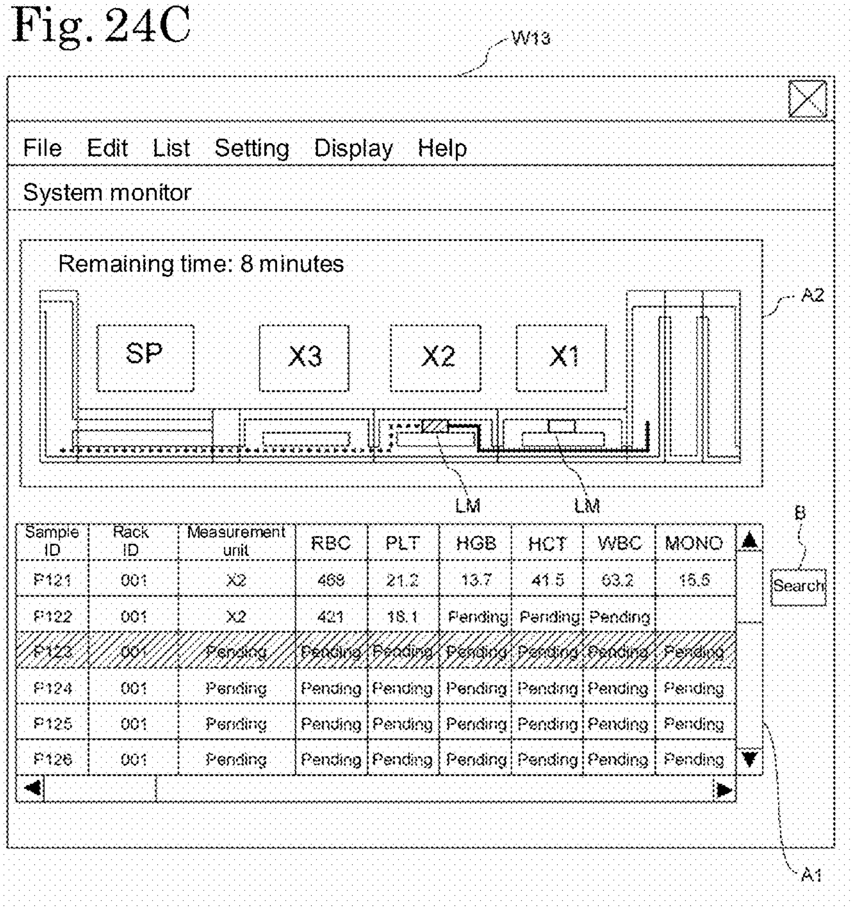
FIG. 24C is a diagram showing one example of the system monitor screen when the sample being measured is in a selected state.

When the user performs the operation of clicking one line of the analysis result list display region A1 from the non-selected state of the sample, such line is selected and the screen display changes to the system monitor screen of the case where the sample being measured is in the selected state (step S703). FIG. 24C is a view showing a system monitor screen of the case where the sample being measured is in the selected state. When one line (third line from the top in FIG. 24C, Line where sample ID is "P123") of the analysis result list display region A1 is selected from the system monitor screen W12 where the sample is in the non-selected state, the line at the uppermost part of the analysis result list display region A1 changes from light blue of temporarily selected color to white of non-selected color, and the selected line third from the top changes from white of non-selected color to blue of selected color.

In the system monitor screen W13, the mark LM of the sample rack L accommodating the selected sample, that is, the rack mark LM displayed at the position of X2-2 has the color in the frame displayed in blue in the processing status display region A2. The display in which the color inside the frame is blue indicates that the information related to the sample accommodated in the sample rack L indicated by the rack mark LM is being selected. Furthermore, in the processing status display region A2, the path through which the sample rack L has already passed indicated by the selected rack mark LM is displayed with a solid line, and the path through which the sample rack L has not passed is displayed with a broken line. The remaining time until the end of processing of the selected sample is also displayed.

Figure 24D:
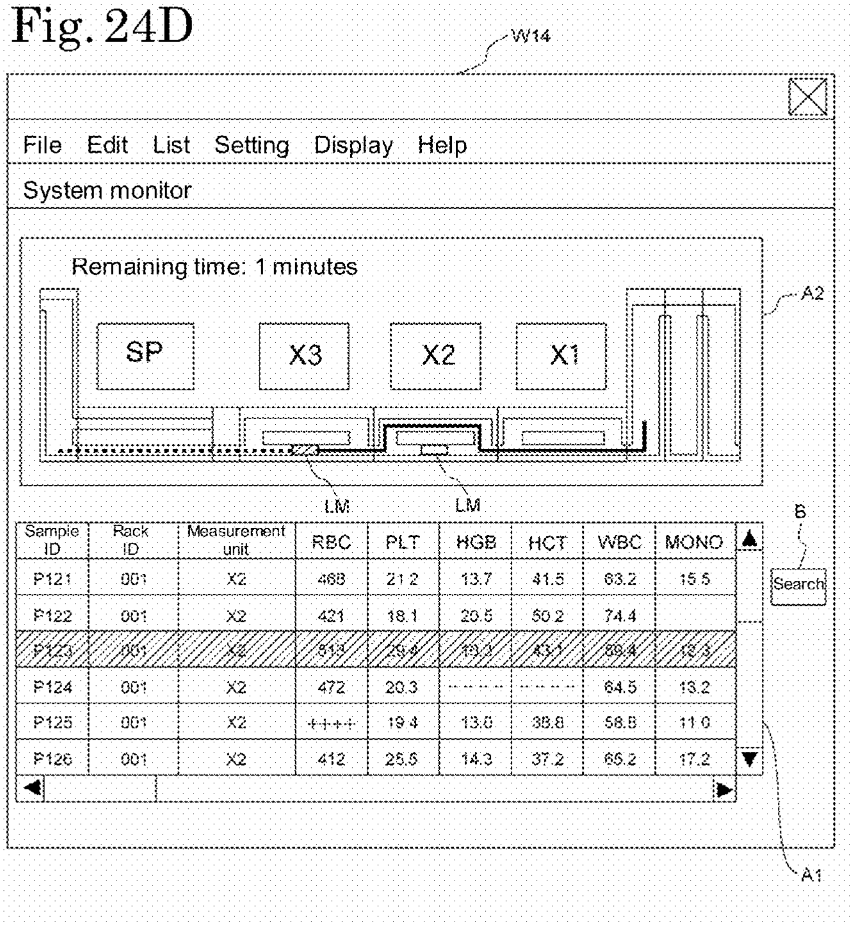
FIG. 24D is a diagram showing one example of the system monitor screen when the sample, which measurement is completed, being conveyed is in a selected state.

After further time has elapsed from such state and the measurement on all the samples accommodated in the sample rack L existing on the sample conveyance device 3 is completed, such sample racks L are conveyed by the sample conveyance device 3, and the screen display changes to the system monitor screen of the case where the sample being conveyed is selected (step S704). FIG. 24D is a view showing the system monitor screen when the sample, which measurement is completed, being conveyed is in the selected state. The sample rack L reaches the skip line L2 of the third sample conveyance device 3 in the conveyance direction as a result of the conveyance of the sample rack L existing on the measurement line L1 of the second sample conveyance device 3 in the conveyance direction, and the sample rack L reaches the skip line L2 of the second sample conveyance device 3 in the conveyance direction as a result of the conveyance of the sample rack L existing on the measurement line L1 of the first sample conveyance device 3 in the conveyance direction. Thus, in the system monitor screen W14 shown in FIG. 24D, the rack marl LM is displayed at the positions X3-3 and X2-3 of the conveyance status display region A2, and the rack marl LM at the position of X3-3 is in the selected state.

The path of the selected rack mark LM of the conveyance status display region A2 is updated, the path on the right side than the rack marl LM is displayed with a solid line indicating passed, and the path on the left side of the rack mark LM is displayed with a broken line indicating non-passed. The display of the remaining time is also updated. Since the analysis of all samples accommodated in the sample rack L being conveyed is completed, the numerical value data of the analysis result is displayed for the information of all samples of the analysis result list display region A1. In FIG. 24D, in the measurement of the HGB and the HCT of the sample having a sample ID of P124, "----" is displayed in the cell of the HGB and the HCT as measurement error occurred, and "++++" is displayed in the cell of the RBC as the numerical value of the measurement result of the RBC of the sample having a sample ID of P125 exceeds the display range.

Figure 24E:
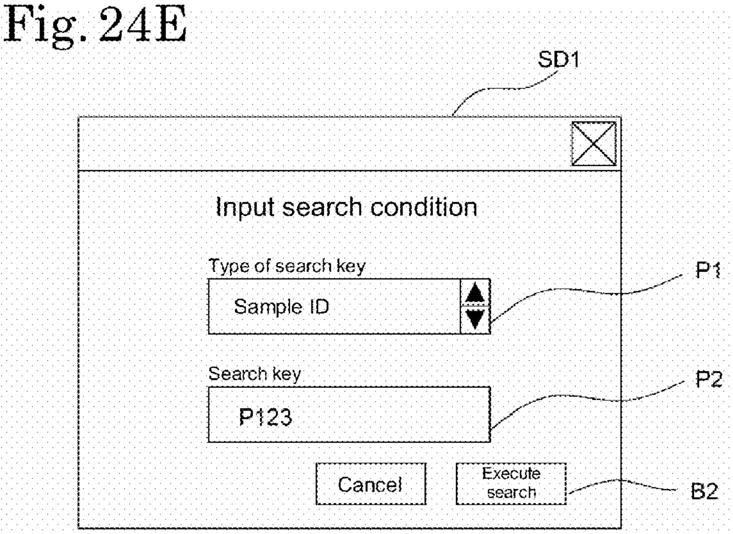
FIG. 24E is a diagram showing one example of the search condition input dialog input with search conditions.
Figure 24F:
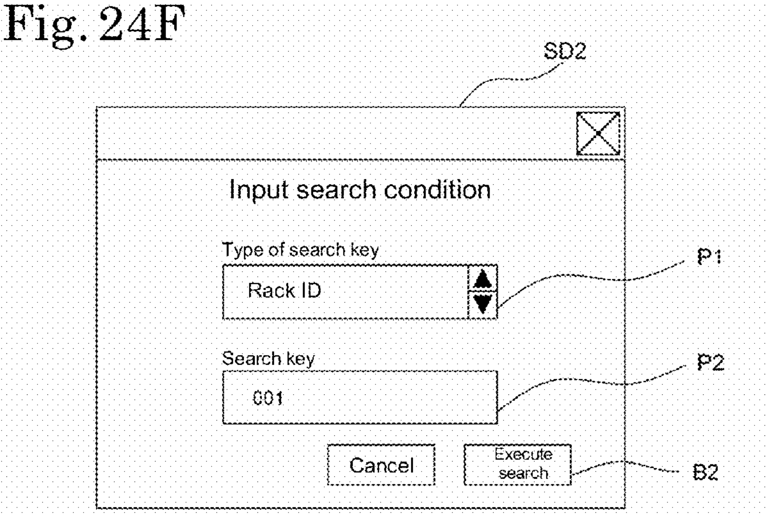
FIG. 24F is a diagram showing another example of the search condition input dialog input with search conditions.

The search condition input dialog is displayed by clicking the search button B of the system monitor screen W14 (step S705). FIGS. 24E and 24F are views showing the search condition input dialog. As shown in FIG. 24E, the "sample ID" is selected as the type of search key in the search condition input dialog SD1 immediately after the display. In FIG. 24E, a state in which "P123" is input to the input box P2 of the search key by the operator is shown.

The search condition input dialog SD2 of a state in which the "rack ID" is selected as the type of search key by the operator is shown in FIG. 24F. In FIG. 24F, a state in which "001" is input to the input box P2 of the search key by the operator is shown.

Figure 24G:
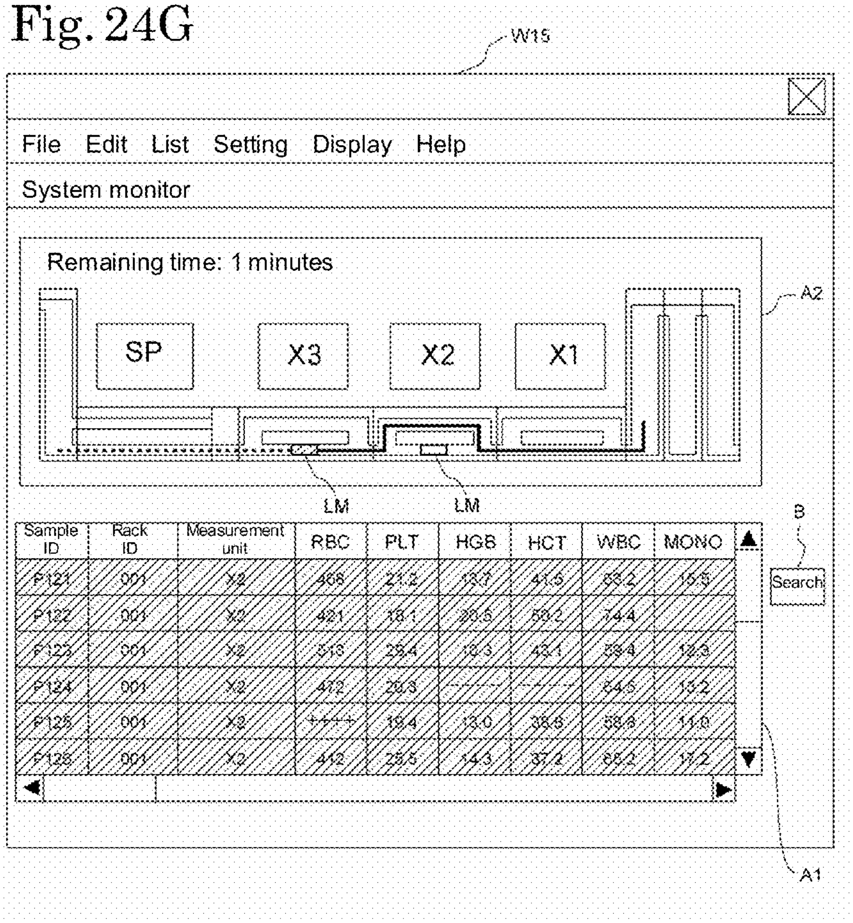
FIG. 24G is a diagram showing one example of the system monitor screen after sample information is searched.

When the search execute button is clicked in the search condition input dialog SD2 of the state shown in FIG. 24F, the system monitor screen W15 in which the information of the sample having the rack ID of "001" is selected is displayed in the analysis result list display region A1 (step S706). FIG. 24G is a view showing the system monitor screen after the sample information is searched. As shown in FIG. 24G, the sample accommodated in the sample rack L having the rack ID of "001" exists in plurals such as samples having the sample ID of "P121" to "P126", where all the sample information related to such samples are selected in the system monitor screen W15. That is, a plurality of lines in the analysis result list display region A1 is displayed in blue. The rack mark LM showing the sample rack L existing in the skip line L2 of the third sample conveyance device 3 in the conveyance direction having the rack ID of "001" is in the selected state and is displayed in blue. Other screen configurations of the system monitor screen W15 are similar to the system monitor screen W14.

Figure 24H:
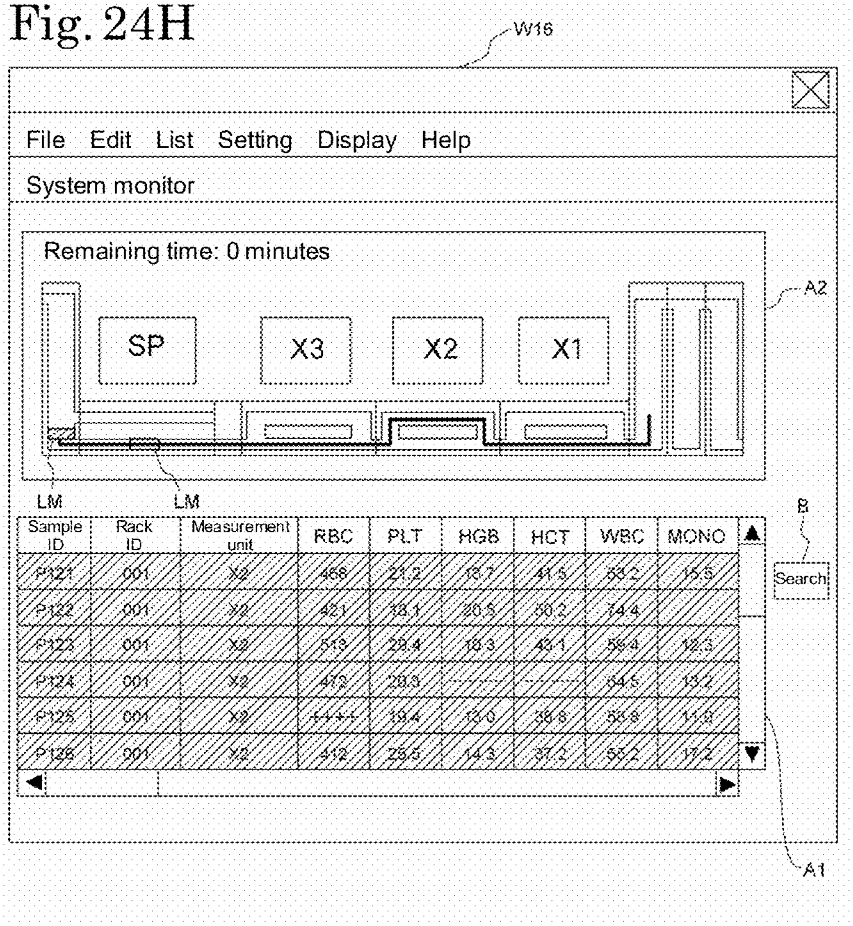
FIG. 24H is a diagram showing one example of the system monitor screen when conveyance of the selected sample is completed.

After time has elapsed and the sample rack L existing on the skip line L2 of the third sample conveyance device 3 in the conveyance direction is accommodated in the sample accommodating device 4, the screen display changes to the system monitor screen of the case where the conveyance of the searched sample is completed (step S707). FIG. 24H is a view showing the system monitor screen of the case where the conveyance of the selected sample is completed. In the system monitor screen W16, the rack mark LM in the selected state is displayed at the position of SKY (see FIG. 14) of the conveyance status display region A2. All the paths leading to the rack mark LM are displayed with a solid line, indicating that the rack has passed all the paths. Furthermore, "0 minutes" is displayed for the remaining time, indicating that the processing of the sample accommodated in the sample rack L is completed. The display of the analysis result list display region A1 of the system monitor screen W16 is similar to the system monitor screen W15, and thus the description will be omitted.

According to the above configuration, the operator can check the analysis results of a plurality of samples all at once by the system monitor screen of the test information managing device 9. With respect to the sample which analysis result is not obtained, it can be understood at a glance that the processing is not completed as the analysis result is not displayed. The operator can select the sample information of the sample which process is not completed from the plurality of samples displayed in a list to check the conveyance status of the relevant sample. The operator can check the history of the processing of the sample by selecting the sample which process is completed.

The layout chart of the sample processing system 1 is displayed in the system monitor screen, wherein the operator can easily understand at which position in the system the sample exists and what kind of process is being performed since the position of the selected sample is displayed on the layout chart. Furthermore, since the path the sample has passed in the past is displayed in the layout chart, with which device the sample has been processed can be understood. Moreover, with which device the sample is to be processed in the future can be understood as the path the sample is scheduled to pass in the future is displayed in the layout chart. The passed path and the non-passed path are displayed with different display formats, so that the operator can easily distinguish the passed path and the non-passed path.

Since the remaining time until the completion of the processing of the selected sample is displayed, the operator can easily check the remaining time when a sample which remaining time until the completion of the process is to be known exists. Since the remaining time until the completion of the process is displayed with the path the sample is scheduled to pass in the future, the operator can grasp how much time is required until the completion of the process by the process of which device.

As the analysis result of the sample can be searched and the search result is displayed in the analysis result list display region A1, the operator can cause the test information managing device 9 to search the analysis result of the sample which analysis result and the conveyance status are to be checked, and easily display the analysis result and the conveyance status (processing history if process is completed) of the sample.

(Other Embodiments)

In the embodiments described above, the system monitor screen W1 includes the analysis result list display region A1 and the conveyance status display region A2. However, the present invention is not limited thereto. For instance, a window displaying the analysis result list may be displayed, the selection of the sample may be accepted in the relevant window, and the conveyance status of the selected sample may be displayed in a window independent from the window of the analysis result list. The analysis result list may be displayed on the screen, the selection of the sample may be accepted from the analysis result list, and the display may be switched from the screen of the analysis result list to the screen displaying the conveyance status of the selected sample.

In the embodiment described above, a configuration of displaying the analysis result list and the conveyance status of the sample in the test information managing device 9 has been described. However, the present invention is not limited thereto. For instance, a configuration of displaying the analysis result list and the conveyance status of the sample in the system control device 8 or the information processing unit 52 may be adopted.

In the embodiment described above, a configuration of displaying "0" for the remaining time when the remaining time of the process of the sample becomes smaller than or equal to zero has been described above. However, the present invention is not limited thereto. For instance, when the remaining time of the process becomes smaller than or equal to zero, the remaining time of a negative number may be displayed. For instance, when the remaining time is "−5 minutes", the operator can look at the display of the remaining time and know that five minutes have elapsed from the completion of the process. The operator thus can grasp the elapsed time after the completion of the process.

In the embodiment described above, a configuration in which the sample processing system 1 includes the blood analyzer 5 for classifying the blood cells contained in the sample and counting the blood cells for every blood cell type has been described above. However, the present invention is not limited thereto. For instance, the sample processing system may include a sample analyzer other than the immune analyzer, the blood coagulation measurement device, the biochemical analyzer, and the urine analyzer, so that the blood sample or the urine sample is conveyed to the measurement unit of the relevant sample analyzer.

In the embodiment described above, a configuration of executing all processes of the computer program 94*a* by the single computer 9*a* has been described. However, the present invention is not limited thereto. For instance, a distributed system of distributing the processes similar to the computer program 94*a* to a plurality of devices (computers) and executing the programs may be adopted.

In the embodiment described above, a configuration in which the sample processing system 1 includes a plurality of devices such as the sample inserting device 2, the sample conveyance devices 3, 301, the sample accommodating device 4, the sample analyzer 5, the smear producing device 6, the system control device 8, and the test information managing device 9 has been described. However, the present invention is not limited thereto. For instance, the sample processing system 1 may be configured by a single device capable of executing the functions of each device.

In the embodiment described above, a configuration in which the system control device 8 determines the conveying destination (measurement unit 51) of the sample rack L inserted to the sample inserting device 2 based on the measurement order received from the test information managing device 9, and the sample conveyance device 3 conveys the sample rack L to the conveying destination determined by the system control device 8 has been described. However, the present invention is not limited thereto. For instance, the system control device 8 may not determine the conveying destination of the sample rack L, and the sample conveyance device 3 may sequentially and evenly convey the sample rack L inserted to the sample inserting device 2 to each of the plurality of measurement units 51.

What is claimed is:

1. A sample processing apparatus comprising:

a plurality of measuring units, each of which measures a sample;

a sample conveyance unit for conveying a sample to at least one of the plurality of measurement units;

a display unit; and a display controller for controlling the display unit to display an analysis result of a sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units;

wherein the display controller controls the display unit to numerically display the analysis result, and to graphically display the conveyance status information; and wherein the display controller controls the display unit to display a layout chart of the sample processing apparatus and a position of the sample on the layout chart as the conveyance status information.

2. The sample processing apparatus of claim 1, wherein the conveyance status information includes conveyance history information indicating a conveyance path through which the sample passed in the past, and conveyance scheduling information indicating a conveyance path through which the sample is to pass in the future.

3. The sample processing apparatus of claim 1, further comprising a determiner for determining a conveying destination of the sample by the sample conveyance unit from the plurality of measurement units; wherein the sample conveyance unit conveys the sample to a measurement unit determined by the determiner as the conveying destination.

4. The sample processing apparatus of claim 1, further comprising a memory for storing a position of the sample in the sample processing apparatus, wherein the conveyance status information of the sample includes the position of the sample stored in the memory.

5. The sample processing apparatus of claim 1, further comprising an input unit, wherein the display controller controls the display unit to display sample specifying information for specifying the sample, which the analysis result has not been obtained yet, and controls the display to display the conveyance status information of the sample when the sample specified by the sample specifying information is selected through the input unit.

6. The sample processing apparatus of claim 5, wherein the display controller controls the display unit to display a search condition input region capable of accepting an input of a search condition for searching a sample;

the sample processing apparatus further includes a retriever for searching for a sample that matches the search condition which has been input to the search condition input region through the input unit; and the display controller controls the display unit to display the search result by the retriever.

7. A sample processing apparatus comprising:

a plurality of measuring units, each of which measures a sample;

a sample conveyance unit for conveying a sample to at least one of the plurality of measurement units;

a display unit; and a display controller for controlling the display unit to display an analysis result of a sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units;

wherein the display controller controls the display unit to display measurement unit specifying information for specifying a measurement unit where the sample, which the analysis result has been obtained, was measured.

8. A sample processing apparatus comprising:

a plurality of measuring units, each of which measures a sample;

a sample conveyance unit for conveying a sample to at least one of the plurality of measurement units;

a display unit;

a display controller for controlling the display unit to display an analysis result of a sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units; and an acquirer for acquiring a time related to elapse of processing of the sample conveyed by the sample conveyance unit, wherein the display controller controls the display unit to display the time related to the elapse of the processing of the sample acquired by the acquirer.

9. The sample processing apparatus of claim 8, wherein the time related to the elapse of the processing of the sample is a remaining time until completion of the processing of the sample.

10. The sample processing apparatus of claim 9, wherein the sample conveyance unit further includes an accommodating portion for accommodating a sample which measurement by at least one of the plurality of measurement units has been terminated; and the remaining time until the completion of the processing of the sample is a time until the sample is accommodated in the accommodating portion.

11. A sample processing apparatus comprising:

a plurality of measuring units, each of which measures a sample;

a sample conveyance unit for conveying a sample to at least one of the plurality of measurement units;

a display unit; and a display controller for controlling the display unit to display an analysis result of a sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units;

wherein the display controller controls the display unit to display sample specifying information for specifying the sample, which the analysis result has been obtained, and the analysis result, and controls the display unit to display conveyance history information indicating a conveyance path through which the sample passed in the past when the sample is selected through the input unit.

12. A sample processing apparatus comprising:

a plurality of measuring units, each of which measures a sample;

a sample conveyance unit for conveying a sample to at least one of the plurality of measurement units; and an information processing unit for displaying information related to a sample including, a display unit, and a display controller for executing a process of controlling the display unit to display an analysis result of a sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units;

wherein the display controller controls the display unit to numerically display the analysis result, and to graphically display the conveyance status information; and wherein the display controller controls the display unit to display a layout chart of the sample processing apparatus and a position of the sample on the layout chart as the conveyance status information.

13. The sample processing apparatus of claim 12, wherein the conveyance status information includes conveyance history information indicating a conveyance path through which the sample passed in the past, and conveyance scheduling information indicating a conveyance path through which the sample is to pass in the future.

14. The sample processing apparatus of claim 12, wherein the information processing unit further includes an input unit; and the controller further executes a process of controlling the display unit to display sample specifying information for specifying the sample, which the analysis result has not been obtained yet, and controlling the display unit to display the conveyance status information of the sample when the sample specified by the sample specifying information is selected through the input unit.

15. The sample processing apparatus of claim 14, wherein the information processing unit further includes a memory for storing a position of the sample in the sample processing apparatus, and the conveyance status information of the sample includes the position stored in the memory.

16. The sample processing apparatus of claim 14, wherein the controller further executes processes of:

(a) controlling the display unit to display a search condition input region capable of accepting an input of a search condition for searching a sample;

(b) searching for a sample that matches the search condition which has been input to the search condition input region through the input unit; and (c) controlling the display unit to selectably display the search result.

17. A sample processing apparatus comprising:

a plurality of measuring units, each of which measures a sample;

a sample conveyance unit for conveying a sample to at least one of the plurality of measurement units; and an information processing unit for displaying information related to a sample including, a display unit, and a controller for executing a process of controlling the display unit to display an analysis result of a sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units wherein the information processing unit further includes an input unit;

wherein the controller further executes a process of controlling the display unit to display the sample specifying information for specifying the sample, which the analysis result has been obtained, and the analysis result, and controlling the display unit to display conveyance history information indicating a conveyance path through which the sample passed in the past when the sample, which the analysis result has been obtained, is selected through the input unit.

18. A sample information display apparatus for displaying information related to a sample processed in a sample processing apparatus including a plurality of measuring units, each of which measures a sample, and a sample conveyance unit for conveying a sample to at least one of the plurality of measurement units, the sample information display apparatus comprising:

a display unit; and a display controller for controlling the display unit to display an analysis result of the sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units;

wherein the display controller controls the display unit to numerically display the analysis result, and to graphically display the conveyance status information; and wherein the display controller controls the display unit to display a layout chart of the sample processing apparatus and a position of the sample on the layout chart as the conveyance status information.

19. A sample information display apparatus for displaying information related to a sample processed in a sample processing apparatus including a plurality of measuring units, each of which measures a sample, and a sample conveyance unit for conveying a sample to at least one of the plurality of measurement units, the sample information display apparatus comprising:

a display unit; and a display controller for controlling the display unit to display an analysis result of the sample which the analysis result has been obtained based on the measurement by at least one of the plurality of measurement units, and controlling the display unit to display conveyance status information indicating a conveyance status of a sample which analysis result has not been obtained yet based on the measurement by at least one of the plurality of measurement units;

wherein the display controller controls the display unit to display measurement unit specifying information for specifying a measurement unit where the sample, which the analysis result has been obtained, was measured.

* * * * *